US009129431B2

(12) United States Patent
Maeda et al.

(10) Patent No.: US 9,129,431 B2
(45) Date of Patent: Sep. 8, 2015

(54) MOTION-TRACKING X-RAY CT IMAGE PROCESSING METHOD AND MOTION-TRACKING X-RAY CT IMAGE PROCESSING DEVICE

(71) Applicant: NATIONAL UNIVERSITY CORPORATION KYOTO UNIVERSITY, Kyoto, Kyoto Prefecture (JP)

(72) Inventors: Shinichi Maeda, Kyoto (JP); Takumi Tanaka, Kyoto (JP); Shin Ishii, Kyoto (JP)

(73) Assignee: National University Corporation Kyoto University, Kyoto (JP)

( * ) Notice: Subject to any disclaimer, the term of this patent is extended or adjusted under 35 U.S.C. 154(b) by 0 days.

(21) Appl. No.: 14/366,037

(22) PCT Filed: Dec. 18, 2012

(86) PCT No.: PCT/JP2012/008088
§ 371 (c)(1),
(2) Date: Jun. 18, 2014

(87) PCT Pub. No.: WO2013/094186
PCT Pub. Date: Jun. 27, 2013

(65) Prior Publication Data
US 2014/0334705 A1 Nov. 13, 2014

(30) Foreign Application Priority Data
Dec. 18, 2011 (JP) ................ 2011-276545

(51) Int. Cl.
G06K 9/00 (2006.01)
G06T 11/00 (2006.01)
(Continued)

(52) U.S. Cl.
CPC ............. *G06T 11/008* (2013.01); *A61B 6/032* (2013.01); *A61B 6/5258* (2013.01);
(Continued)

(58) Field of Classification Search
USPC ......................................................... 382/131
See application file for complete search history.

(56) References Cited

U.S. PATENT DOCUMENTS 8,401,252 B2 * 3/2013 Schneiderman et al. ..... 382/118
8,824,756 B2 9/2014 Joshi et al.
(Continued)

OTHER PUBLICATIONS

H. I. Goldberg et al., "Evaluation of ultrafast CT scanning of the adult abdomen," Invest. Radiol., 24, 537-543, 1989.
C. C. Morehouse et al., "Gated cardiac computed tomography with a motion phantom," Radiology 134, 213-217, 1980.
(Continued)

*Primary Examiner* — John Strege
(74) *Attorney, Agent, or Firm* — Ogilvie Law Firm

(57) ABSTRACT

An x-ray CT image processing method which carries out a statistical estimate in prior knowledge relating to the movement and the x-ray absorption coefficient of a measurement subject comprises: a step of hypothesizing that the measurement subject changes smoothly over time, and defining a first probability model (prior knowledge of the measurement subject over all times) relating to movement and a second probability model (projected image observation model over all times) relating to observation; and a step of carrying out a statistical estimate dependent on both the first probability model and the second probability model. The first probability model relating to the movement of the measurement subject and the second model relating to observation are defined as probability models with which statistical estimates are carried out at the outset, and motion and CT images are simultaneously estimated by carrying out induction based on the probability models.

13 Claims, 9 Drawing Sheets

(51) Int. Cl.
*A61B 6/03* (2006.01)
*G06T 7/00* (2006.01)
*G06T 7/20* (2006.01)
*A61B 6/00* (2006.01)

(52) U.S. Cl.
CPC .............. *G06T 7/0012* (2013.01); *G06T 7/20* (2013.01); *G06T 7/208* (2013.01); *G06T 11/005* (2013.01); *A61B 6/503* (2013.01); *G06T 2207/10081* (2013.01); *G06T 2207/20076* (2013.01); *G06T 2207/30048* (2013.01); *G06T 2211/412* (2013.01)

(56) References Cited

U.S. PATENT DOCUMENTS

| | | | | |
|---|---|---|---|---|
| 2005/0105682 | A1* | 5/2005 | Heumann et al. | 378/58 |
| 2006/0067461 | A1* | 3/2006 | Yin et al. | 378/5 |
| 2010/0138379 | A1* | 6/2010 | Mott et al. | 706/52 |
| 2011/0268335 | A1* | 11/2011 | Kunze et al. | 382/131 |
| 2013/0287278 | A1* | 10/2013 | Olivier et al. | 382/131 |

OTHER PUBLICATIONS

P. M. Joseph and J. Whitley, "Experimental simulation evaluation of ECG-gated heart scans with a small number of views," Med. Phys. 10, 444-449, 1983.

B. Ohnesorge et al., "Cardiac imaging by means of electrocardiographically gated multisection spiral CT: initial experience," Radiology 217, 564-571, 2000.

C. J. Ritchie et al.,"Correction of computed tomography motion artifacts using pixel specific back-projection," IEEE Trans. Med. Imaging 15, 333-342, 1996.

G. Wang et al., "A knowledge-based cone-beam x-ray CT algorithm for dynamic volumetric cardiac imaging," Med Phys. 29(8), 1807-1822, 2002.

K. Taguchi et al., "Toward time resolved cardiac CT images with patient dose reduction: image-based motion estimation", Nuclear Science Symposium Conference Record, 4, 2029-2032, 2006.

AA. Isola et al., "Fully automatic nonrigid registration-based local motion estimation for motion-corrected iterative cardiac CT reconstruction," Med Phys. 37(3), 1093-1109 2010.

AA. Isola et al., "Motion compensated iterative reconstruction of a region of interest in cardiac cone-beam CT" Comput. Med. Imag. Grap. 34(2), 149-159 2010.

* cited by examiner

Z : Tissue class
x : True image
y : Projection
B : Hidden variable to control a prior distribution (1) true (2) FBP(21.57dB)

(3) Absence of B (38.35dB)

(4) Presence of B (39.14dB)

(5)

MOTION-TRACKING X-RAY CT IMAGE PROCESSING METHOD AND MOTION-TRACKING X-RAY CT IMAGE PROCESSING DEVICE

TECHNICAL FIELD

The present invention relates to an X-ray CT algorithm capable of tracking a motion of a measuring target, a program having the algorithm, and an X-ray CT device on which the program is installed.

BACKGROUND ART

An X-ray CT is a powerful technique capable of acquiring an internal structure in a noninvasive and nondestructive manner and is being used for a wide range of medical purposes and industrial purposes such as defect inspection. The X-ray CT has been used for reconstructing an internal structure (CT image) based on the assumption that an object targeted for acquisition of its internal structure is at a standstill. However, objects targeted for X-ray CT for medical purposes include hearts, blood vessels, lungs and infants that find difficulty in stopping their motions completely. Applying an X-ray CT algorithm assuming a standstill to such active objects like in a conventional way is known to generate false images called motion artifacts.

Cardiac diseases have been requested to be dealt with in Japan and countries except Japan: cardiac diseases such as cardiac infarction and cardiac angina have been the second leading cause for deaths in Japan and heart diseases have been the leading cause for deaths in the U.S. in these 10 years. Finding lesions of hearts in an early stage is considered to be one of the most effective countermeasures. Accordingly, reconstructing accurate CT images has especially been desired in the field of X-ray CT on hearts.

A technique of reducing motion artifacts conventionally suggested has been targeted mainly for hearts in terms of significance of its application. As an example, according to known prior-art 1 (see non-patent literature 1, for example) shown in FIG. 14 in the field of X-ray CT targeted for hearts, an imaging target is scanned at high speed to shorten imaging time, thereby reducing motion artifacts. According to known prior-art 2 (see non-patent literatures 2-4, for example) shown in FIG. 15, a CT image is reconstructed by synchronizing a cardiac phase based on an electrocardiogram. According to known prior-art 3 (see non-patent literatures 5-9, for example), a CT image is reconstructed by correcting a motion based on estimation of the motion of a heart.

A more intense X-ray leads to a higher SN ratio of a reconstructed image, resulting in a trade-off between reduction in a dose of exposure with an X-ray and the SN ratio. Techniques of acquiring a reconstructed image having an SN ratio substantially the same as conventional one with a lower dose of exposure with an X-ray include: a technique intended to enhance a resolution capable of acquiring an image of a higher resolution with an X-ray intensity and the number of captured images same as a conventional intensity and a conventional number; a technique intended to shorten imaging time capable of shortening imaging time by reducing the number of captured images with an X-ray intensity and a resolution same as a conventional intensity and a conventional resolution; a technique intended to reduce an exposure dose capable of reducing an exposure dose by reducing an X-ray intensity with a resolution same as a conventional resolution; a technique intended to remove noise capable of reducing noise in a reconstructed image with an X-ray intensity and a resolution same as a conventional intensity and a conventional resolution; a technique intended to enhance a contrast resolving power (indicating the number of applicable tones of a reconstructed image, specifically the accuracy of X-ray absorption coefficients) of the reconstructed image with an X-ray intensity and a resolution same as a conventional intensity and a conventional resolution.

The aforementioned conventional techniques are roughly divided into two: one that makes statistical estimation and one that does not perform statistical estimation. A filtered back projection (FBP; Filtered Back Projection) method forming the mainstream of an image reconstruction method is known as the conventional technique that does not perform statistical estimation. Projection images are obtained through the irradiation of X-ray to the imaging target from various directions. According to the FBP image reconstruction method, the resultant projection images are projected in reverse directions to the irradiation direction in order to reconstruct an X-ray absorption image. In this reconstruction, the sinogram is filtered in a frequency range to remove blur.

Where multiple projection images such as CT images can be prepared by capturing images of an object targeted for imaging from different positions or angles, processing information about these projection images is known to enable reconstruction of a cross-sectional image of the original object. A MAP (maximum a posteriori) estimation method and a Bayesian estimation method are known as conventional techniques to perform statistical estimation belonging to image reconstruction methods of restoring a cross-sectional image of an original object using a projection image.

[Non-patent literature 1] H. I. Goldberg et al., "Evaluation of ultrafast CT scanning of the adult abdomen," Invest. Radiol., 24, 537-543, 1989.

[Non-patent literature 2] C. C. Morehouse et al., "Gated cardiac computed tomography with a motion phantom," Radiology 134, 134-137, 1980.

[Non-patent literature 3] P. M. Joseph and J. Whitley, "Experimental simulation evaluation of ECG-gated heart scans with a small number of views," Med. Phys. 10, 444-449, 1983.

[Non-patent literature 4] B. Ohnesorge et al., "Cardiac imaging by means of electrocardiographically gated multisection spiral CT: initial experience," Radiology 217, 564-571, 2000.

[Non-patent literature 5] C. J. Ritchie et al., "Correction of computed tomography motion artifacts using pixel specific back-projection," IEEE Trans. Med. Imaging 15, 333-342, 1996.

[Non-patent literature 6] G. Wang et al., "A knowledge-based cone-beam x-ray CT algorithm for dynamic volumetric cardiac imaging," Med Phys. 29(8), 1807-1822, 2002.

[Non-patent literature 7] K. Taguchi et al., "Toward time resolved cardiac CT images with patient dose reduction: image-based motion estimation", Nuclear Science Symposium Conference Record, 4, 2029-2032, 2006.

[Non-patent literature 8] AA. Isola et al., "Fully automatic nonrigid registration-based local motion estimation for motion-corrected iterative cardiac CT reconstruction," Med Phys. 37(3), 1093-1109 2010.

[Non-patent literature 9] AA. Isola et al., "Motion compensated iterative reconstruction of a region of interest in cardiac cone-beam CT" Comput. Med. Imag. Grap. 34(2), 149-159 2010.

OUTLINE OF THE INVENTION

Problems to be Solved by the Invention

Rotating an X-ray source at high speed like in the aforementioned prior-art 1 increases centrifugal force. This makes it hard to design the X-ray source such that the X-ray source can withstand such physical force, so that increasing the rotation speed of the X-ray source has actually plateaued. A speed achieved at present is such that the X-ray source finishes a half cycle in about 2.5 seconds (one cycle in about 0.5 seconds). Meanwhile, one cycle of the heart rate is about one second and the volume of a heart changes largely in about 0.25 seconds. Accordingly, making an assumption that a heart is an inactive part like in the aforementioned prior-art 1 should always become unfeasible.

Like in the aforementioned prior-art 2, according to the technique of taking an electrocardiogram simultaneously with X-ray CT on a heart and reconstructing an image only of a specific phase using only a projection image acquired when the heart rate becomes the same phase, only the projection image acquired to coincide with the specific timing is used. This unfortunately results in an exposure dose higher than usual.

Like in the aforementioned prior-art 3, according to the technique of acquiring a projection image of the same coordinate phase so as to coincide with timing of taking an electrocardiogram and estimating a CT image of a different cardiac phase as one about an active object based on an X-ray CT image reconstructed from the acquired projection image, change in the length of one cycle of a heart is permitted. Meanwhile, this technique specifies a cardiac phase at a given time on the assumption that the heart is subjected to the same volume change in every one cycle. However, the prior-art 3 actually finds difficulty in matching phases accurately for an area of a rapid motion, for example. The prior-art 3 also encounters an additional problem resulting from the fact that a heart inherently does not make the same motion in every instant of time. Additionally, parts such as blood vessels may shift their positions in response to each cardiac beat. In particular, change in the volume of a heart is known to follow a course differing between the case where the heart beats short and the case where the heart beats long. The prior-art 3 suffers from artifacts due to these factors. The prior-art 3 further suffers from a problem in that motion artifacts cannot be prevented as a motion responsive to breathing becomes unavoidable for a patient who cannot hold his or her breath.

It is therefore an object of the present invention to provide a motion tracking X-ray CT image processing method and a motion tracking X-ray CT image processing device capable of reducing motion artifacts compared to image reconstruction using prior art by estimating a motion and a CT image simultaneously.

Means to Solve the Objects

In view of the aforementioned circumstances, the motion tracking X-ray CT image processing method of the present invention makes statistical estimation based on prior knowledge about a motion and X-ray absorption coefficients of a measuring target. The method includes: a step of defining a first probability model relating to a motion (prior knowledge about the measuring target in every instant of time) and a second probability model relating to observation (observed model of a projection image in every instant of time), the first and second probability models being defined on the assumption that the measuring target changes smoothly with time; and a step of making statistical estimation depending on both the first and second probability models.

This structure defines the first probability model relating to a motion of the measuring target (prior knowledge about the measuring target in every instant of time) and the second probability model relating to observation (observed model of a projection image in every instant of time). The first and second probability models are defined as probability models to be inherently used for statistical estimation. Then, an inference is drawn based on these probability models. This makes it possible to estimate both a motion and a CT image simultaneously without requiring synchronization with an electrocardiogram, for example.

Estimation based on a probability model enables us to use a reliable estimation framework established in statistics where the convergent and consistent estimators are easily constructable.

Specifically, in the conventional technique, a motion is estimated depending on a model relating to a motion based only on a resultant CT reconstructed image (conventional technique employs a deterministic model), and a CT reconstructed image is estimated depending only on an observed model based on the resultant motion. In contrast, the present invention achieves estimation of higher accuracy by estimating both a CT reconstructed image and a motion simultaneously while considering both a probability model about a motion and a probability model about observation.

Using a probability model to perform statistical estimation easily allows incorporation of other prior knowledge, leading to enhancement of the quality of image reconstruction.

It is preferable that the first probability model (prior knowledge about the measuring target in every instant of time) be expressed by a first probability distribution characterized by a parameter defined for each pixel of a reconstructed image. The parameter expresses a degree of temporal continuity of the reconstructed image. On the assumption that the reconstructed image is a known image, it is preferable that the second probability model (observed model of a projection image in every instant of time) be expressed by a second probability distribution that describes a projection image expected to be observed from the reconstructed image.

The first probability model is expressed by the first probability distribution characterized by the parameter expressing a degree of temporal continuity of the reconstructed image. This means that different reconstructed images are assumed in different instants of time and temporally smooth deformations of these reconstructed image in different instants of time are expressed in the form of a probability distribution.

It is preferable that the first probability distribution be further characterized by adding a term expressing spatial correlation between neighboring pixels of the reconstructed image.

It is preferable that the first probability distribution be further characterized by a probability distribution showing that each pixel value of the reconstructed image is likely to take on a specific value depending on a tissue and a probability distribution showing that a tissue is also displaced temporally continuously.

On the assumption that a reconstructed image in each instant of time is a known image, the second probability model is expressed in the form of a probability distribution including information about a projection image expected to be observed from the reconstructed image.

In the motion tracking X-ray CT image processing method of the present invention, it is preferable that the first probability distribution be further characterized by a probability distribution showing that each pixel value of the reconstructed image is likely to take on a specific value depending on a tissue and a probability distribution showing that a tissue is also displaced temporally continuously.

In the motion tracking X-ray CT image processing method of the present invention, it is further preferable that the first probability distribution be further characterized by expressing a tissue class with a hidden state variable given to each pixel of the reconstructed image. Specifically, the first probability distribution is further characterized with a probability variable that shows a tissue class to characterize the reconstructed image further. The probability variable showing a tissue class is given for each pixel of the reconstructed image and shows X-ray absorption coefficients of a tissue (normal cell such as muscle, soft cell such as fat, bone or the like) if an imaging target is a human body, for example. Temporally smooth deformation of the reconstructed image is expressed by the first probability distribution. This deformation can be expressed in the form of a probability distribution assuming that reconstructed images in corresponding instants of time have direct temporal correlation. Alternatively, this deformation can be expressed indirectly through a tissue class by assuming that a tissue class in each instant of time is displaced temporally smoothly. Additionally, distribution information is expressed in the form of a probability distribution indicating a ratio of distribution of each tissue and indicating how easily each tissue can be distributed spatially continuously.

Prior knowledge about a tissue distribution can use a fixed average parameter. Meanwhile, changing this prior knowledge appropriately according to differences among individuals in physique, preexisting physical condition, sex, or age or according to imaging areas can contribute to further enhancement of accuracy in image reconstruction and tissue estimation.

In the motion tracking X-ray CT image processing method of the present invention, it is preferable that the first probability distribution be further characterized with a hidden state variable that expresses a tissue class to which each pixel belongs.

As a result of the presence of the hidden stage variable to control a distribution of a tissue class to which each pixel belongs, the following cases become scarcely influential: the case where an assumed value of X-ray absorption coefficients of a previously assumed tissue class largely shifts from an actual X-ray absorption coefficient of the tissue class, and the case where there is a tissue class not having been assumed. Using the hidden state variable for statistical estimation can control a degree of influence exerted by prior knowledge of the existence of a tissue-dependent CT value on a reconstructed image as a solution to be estimated.

In the motion tracking X-ray CT image processing method of the present invention, it is preferable that the Boltzmann distribution be used as a prior distribution of the aforementioned tissue class.

The Boltzmann distribution is used as a prior distribution of each tissue for the reasons as follows. The measuring target is assumed to change smoothly with time, so that a tissue should also be assumed to change smoothly with time between neighboring frames. Then, attention is given to the fact that the Boltzmann distribution can express this assumption easily by means of temporal correlation of tissue classes in neighboring frames. The Boltzmann distribution has additional characteristics that simultaneously enable expression of spatial continuity of a tissue to be satisfied by the tissue and expression of a likelihood of a ratio of a tissue. A parameter indicating the strength of temporal correlation, the strength of spatial correlation, or a standard existing ratio can be adjusted for each tissue class manually by an expert or through study conducted using ease of application to actual projection data as a reference.

The Gaussian distribution can be used appropriately as a parameter distribution expressing the value of X-ray absorption coefficients typical of each tissue. The Boltzmann distribution can be used appropriately as a parameter distribution expressing a degree of spatial continuity of each tissue. If the hidden state variable to control a distribution of a tissue class is introduced, the mixture Gaussian distribution corresponding to a weighted sum of the Gaussian distributions can be used appropriately as a parameter distribution expressing X-ray absorption coefficients of each tissue.

More specifically, in the aforementioned motion tracking X-ray CT image processing method of the present invention, the statistical estimation is conducted by estimation using a value to maximize a posterior probability (MAP estimation) or by the Bayesian estimation using an expectation of a posterior probability.

The MAP estimation estimates a combination of a maximum likelihood in a posterior distribution relating to both a tissue to which each pixel region of a reconstructed image belongs and X-ray absorption coefficients. Estimating a combination with the tissue to which each pixel region of the reconstructed image belongs means inclusion of tissue class dependence. Including the tissue class dependence can include knowledge depending on a tissue class showing that pixels in an air tissue class can be coupled easily (no tissue can mix into air), for example. This enables distribution expression having a better fit to an actual situation and eventually, this is expected to enhance accuracy in estimating a solution. The MAP estimation allows omission of integration calculation required to obtain a posterior probability of a reconstructed image. This can facilitate optimization, so that a reconstructed image can be obtained at a higher speed.

For estimation of a posterior distribution relating to both X-ray absorption coefficients and a tissue to which each pixel region of a reconstructed image belongs, the Bayesian estimation (approximate Bayesian estimation) makes approximation using a test distribution that can approximate a posterior distribution satisfactorily. Like the MAP estimation, the Bayesian estimation can include tissue class dependence. This enables more flexible distribution expression. The Bayesian estimation enables an inference drawn in consideration of uncertainty of estimation and facilitates parameter study, thereby allowing more accurate X-ray CT image processing.

According to a different aspect of the present invention, the motion tracking X-ray CT image processing method of the present invention includes the following steps 1) to 5).

1) A step of entering measuring conditions including a projection image and at least an X-ray intensity 2) A step of defining physical process about photons observed in the projection image by a probability distribution 3) A step of defining a first probability model relating to a motion of a measuring target (prior knowledge about the measuring target in every instant of time) by a first probability distribution on the assumption that the measuring target changes smoothly with time, the first probability distribution being characterized by a parameter that expresses a degree of temporal continuity of the measuring target 4) A step of defining a second probability model relating to observation (observed model of a projection image in every instant of time) by a second probability distribution on the assumption that a reconstructed image is a known image, the second probability distribution describing a projection image expected to be observed from the reconstructed image 5) A step of reconstructing an image and estimating a tissue class by estimating an expectation of a posterior probability (Bayesian estimation) or by estimating maximization of a posterior probability (MAP estimation) depending on both the first and second probability models The probability distribution defining the physical process about photons mentioned in the aforementioned step 2) is specifically expressed for example by the Poisson distribution defining a probability model about photons observed in a projection image. This enables expression of the physical process more approximate to actual observation process, so that uncertainty of observation due, for example, to photon noise can be expressed.

This description further applies to the descriptions of the aforementioned steps 3) to 5).

The motion tracking X-ray CT image processing device of the present invention is described next.

The motion tracking X-ray CT image processing device of the present invention makes statistical estimation based on prior knowledge about a motion and X-ray absorption coefficients of a measuring target. The device includes: model defining means that defines a first probability model relating to a motion (prior knowledge about the measuring target in every instant of time) and a second probability model relating to observation (observed model of a projection image in every instant of time), the first and second probability models being defined on the assumption that the measuring target changes smoothly with time; and statistically estimating means that makes statistical estimation depending on both the first and second probability models.

It is preferable that the first probability model (prior knowledge about the measuring target in every instant of time) be expressed by a first probability distribution characterized by a parameter defined for each pixel of a reconstructed image. The parameter expresses a degree of temporal continuity of the reconstructed image. On the assumption that the reconstructed image is a known image, it is preferable that the second probability model (observed model of a projection image in every instant of time) be expressed by a second probability distribution that describes a projection image expected to be observed from the reconstructed image.

The first probability model is expressed by the first probability distribution characterized by the parameter expressing a degree of temporal continuity of the reconstructed image. This means that different reconstructed images are assumed in different instants of time and temporally smooth deformations of these reconstructed image in different instants of time are expressed in the form of a probability distribution.

It is preferable that the first probability distribution be further characterized by adding a term expressing spatial correlation between neighboring pixels of the reconstructed image.

It is also preferable that the first probability distribution be further characterized by a probability distribution showing that each pixel value of the reconstructed image is likely to take on a specific value depending on a tissue and a probability distribution showing that a tissue is also displaced temporally continuously.

On the assumption that a reconstructed image in each instant of time is a known image, the second probability model is expressed in the form of a probability distribution including information about a projection image expected to be observed from the reconstructed image.

Like in the aforementioned motion tracking X-ray CT image processing method of the present invention, in the motion tracking X-ray CT image processing device of the present invention, it is preferable that the first probability distribution be further characterized by a probability distribution showing that each pixel value of the reconstructed image is likely to take on a specific value depending on a tissue and a probability distribution showing that a tissue is also displaced temporally continuously.

In the motion tracking X-ray CT image processing device of the present invention, it is further preferable that the first probability distribution be further characterized by expressing a tissue class with a hidden state variable given to each pixel of the reconstructed image. Specifically, the first probability distribution is further characterized with a probability variable that shows a tissue class to characterize the reconstructed image further. The probability variable showing a tissue class is given for each pixel of the reconstructed image and shows X-ray absorption coefficients of a tissue (normal cell such as muscle, soft cell such as fat, bone or the like) if an imaging target is a human body, for example. Temporally smooth deformation of the reconstructed image is expressed by the first probability distribution. This deformation can be expressed in the form of a probability distribution assuming that reconstructed images in corresponding instants of time have direct temporal correlation. Alternatively, this deformation can be expressed indirectly through a tissue class by assuming that a tissue class in each instant of time is displaced temporally smoothly. Additionally, distribution information is expressed in the form of a probability distribution indicating a ratio of distribution of each tissue and indicating how easily each tissue can be distributed spatially continuously.

Prior knowledge about a tissue distribution can use a fixed average parameter. Meanwhile, changing this prior knowledge appropriately according to differences among individuals in physique, preexisting physical condition, sex, or age or according to imaging areas can contribute to further enhancement of accuracy in image reconstruction and tissue estimation.

According to a different aspect of the present invention, the motion tracking X-ray CT image processing device of the present invention includes the following means 1) to 5).

1) Means that enters measuring conditions including a projection image and at least an X-ray intensity 2) Means that defines physical process about photons observed in the projection image by a probability distribution 3) Means that defines a first probability model relating to a motion of a measuring target (prior knowledge about the measuring target in every instant of time) by a first probability distribution on the assumption that the measuring target changes smoothly with time, the first probability distribution being characterized by a parameter that expresses a degree of temporal continuity of the measuring target 4) Means that defines a second probability model relating to observation (observed model of a projection image in every instant of time) by a second probability distribution on the assumption that a reconstructed image is a known image, the second probability distribution describing a projection image expected to be observed from the reconstructed image 5) Means that reconstructs an image and estimates a tissue class by estimating an expectation of a posterior probability (Bayesian estimation) or by estimating maximization of a posterior probability (MAP estimation) depending on both the first and second probability models The probability distribution defining the physical process about photons mentioned in the aforementioned means 2) is specifically expressed for example by the Poisson distribution defining a probability model about photons observed in a projection image. This enables expression of the physical process more approximate to actual observation process, so that uncertainty of observation due, for example, to photon noise can be expressed.

A motion tracking X-ray CT image processing program of the present invention makes statistical estimation based on prior knowledge about a motion and X-ray absorption coefficients of a measuring target. The program makes a computer execute the following steps 1) to 5).

1) A step of entering measuring conditions including a projection image and at least an X-ray intensity 2) A step of expressing physical process about photons observed in the projection image by a probability distribution 3) A step of defining a first probability model relating to a motion of a measuring target (prior knowledge about the measuring target in every instant of time) by a first probability distribution that is characterized by a parameter that defines a degree of temporal continuity of a reconstructed image in each instant of time 4) A step of defining a second probability model relating to observation (observed model of a projection image in every instant of time) by a second probability distribution on the assumption that a reconstructed image is a known image, the second probability distribution describing a projection image expected to be observed from the reconstructed image 5) A step of reconstructing an image and estimating a tissue class by estimating an expectation of a posterior probability (Bayesian estimation) or by estimating maximization of a posterior probability (MAP estimation) depending on both the first and second probability models The present invention can further provide an X-ray CT image processing device on which the aforementioned motion tracking X-ray CT image processing program is installed.

Effects of the Invention

The motion tracking X-ray CT image processing method and the motion tracking X-ray CT image processing device of the present invention achieve the effect of reducing motion artifacts compared to image reconstruction using prior art by estimating a motion and a CT image simultaneously. Adopting the estimation method based on the assumption that a measuring target is deformed temporally smoothly eliminates the need for synchronization with an electrocardiogram, for example. This enables dealing with an unexpected body motion or an unexpected motion of an internal organ that cannot be synchronized for example with an electrocardiogram. This further enables estimation using a projection image in every instant of time, so that reduction in an exposure dose is expected.

BEST MODE FOR CARRYING OUT THE INVENTION

Embodiments of the present invention will be described in detail below with reference to the drawings. The present invention is not limited to the following embodiment and examples of shown in the figure, and the present invention can be variously changed in design.

A motion tracking X-ray CT image processing method and an X-ray CT image processing program of the present invention are to reconstruct an image using statistical estimation based on prior knowledge about a motion and X-ray absorption coefficients.

Figure 1:
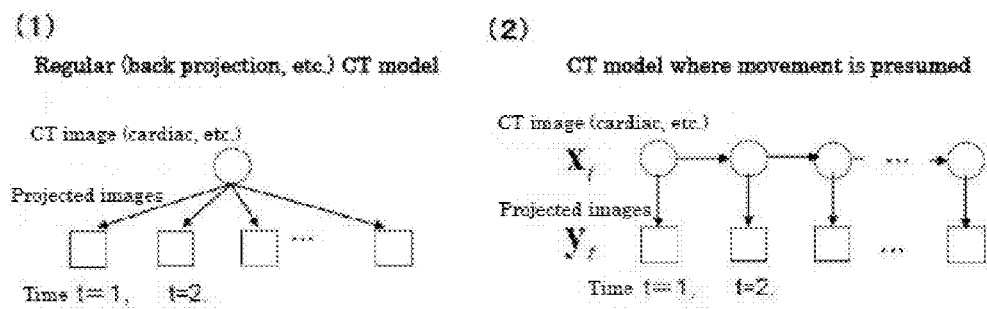
FIG. 1 shows an explanatory view showing a general CT model and a CT model assuming a motion.

A general CT model and a CT model assuming a motion are described by referring to FIG. 1. As shown in FIG. 1(1), in the case of a CT model of a conventional filtered back projection (FBP) method, even if a measuring target is an active object such as a heart, acquiring projection is considered to be permitted from one target (CT image) on the assumption that the target is at a standstill. The present invention starts from the assumption that a measuring target is a moving object and considers that projections can be achieved from different moving targets as shown in FIG. 1(2).

It is assumed that a measuring target at a standstill or a measuring target that changes periodically is not subjected to projection but a measuring target changes smoothly with time. Based on this assumption, a probability model is formulated.

Figure 2:
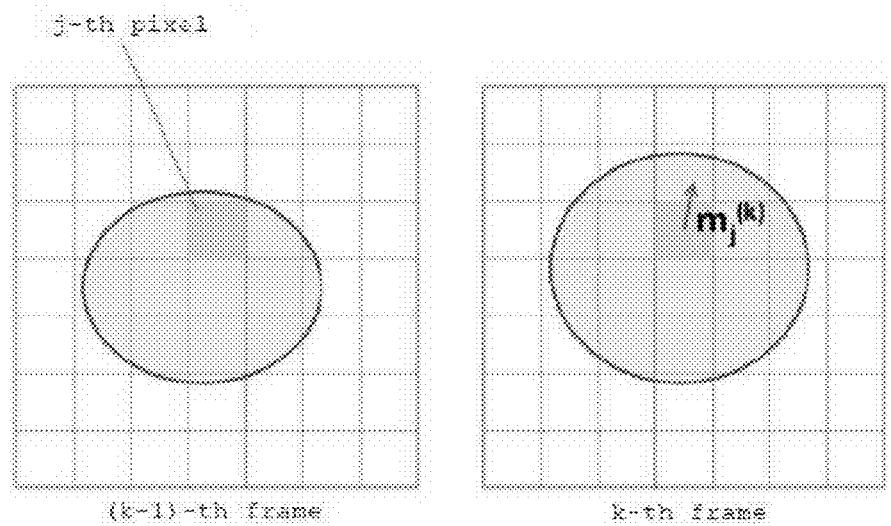
FIG. 2 shows an explanatory view showing a motion of pixels between neighboring frames.

Assuming that the measuring target changes smoothly with time means setting a motion (deformation) parameter for each pixel of a CT image and estimating a motion (deformation) of each pixel between neighboring frames. More specifically, as shown in FIG. 2, a motion of a j-th pixel between reconstructed images of different instants of time ((k−1)-th frame and k-th frame) is expressed by a vector $m_j^{(k)}$.

The following describes projection performed on a measuring target that changes smoothly with time in the form of a statistical model and explains that an image can be reconstructed by making the Bayesian estimation based on this statistical model.

Figure 3:
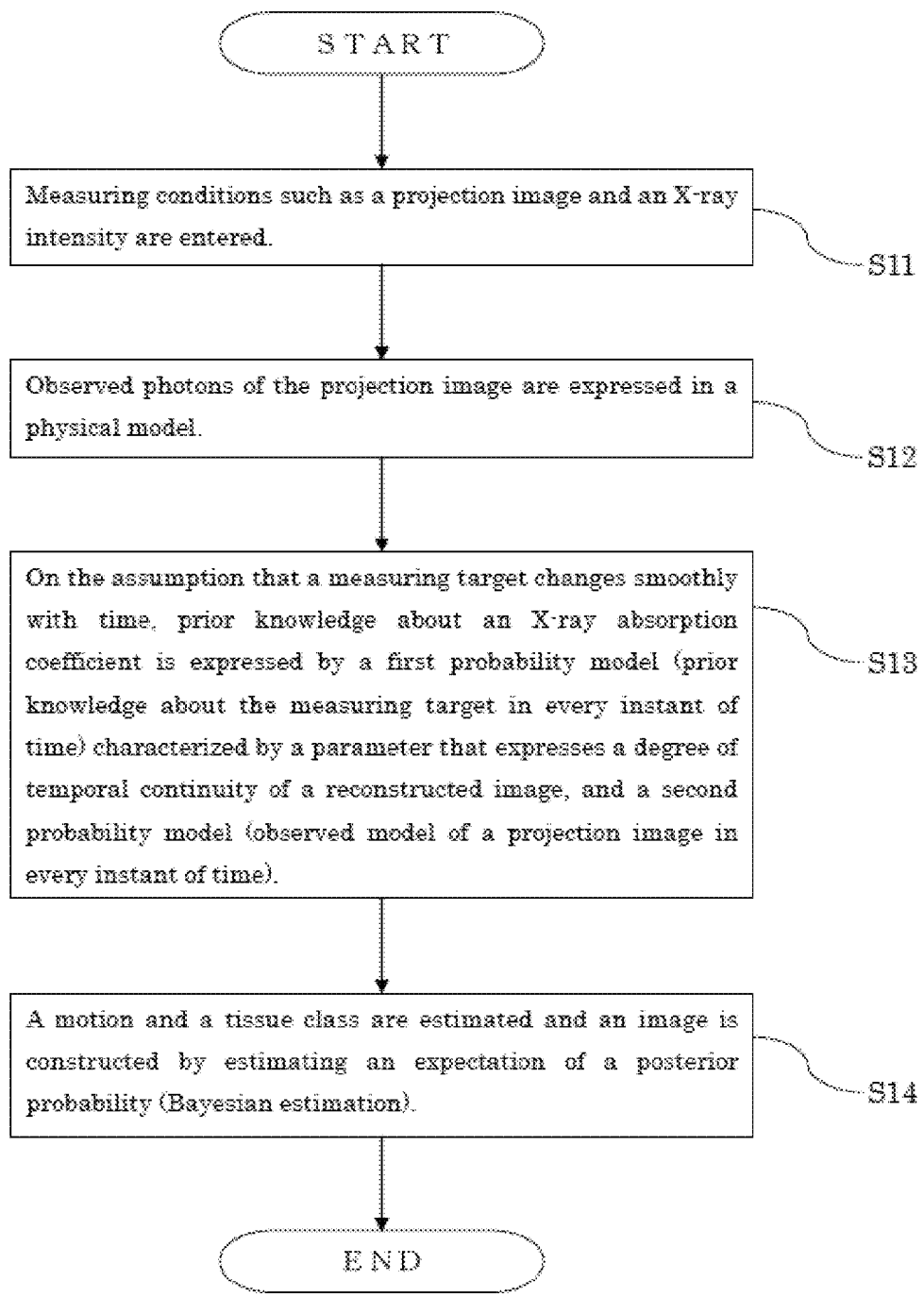
FIG. 3 shows a flow diagram (1) of a motion tracking X-ray CT image processing method of the present invention.
Figure 4:
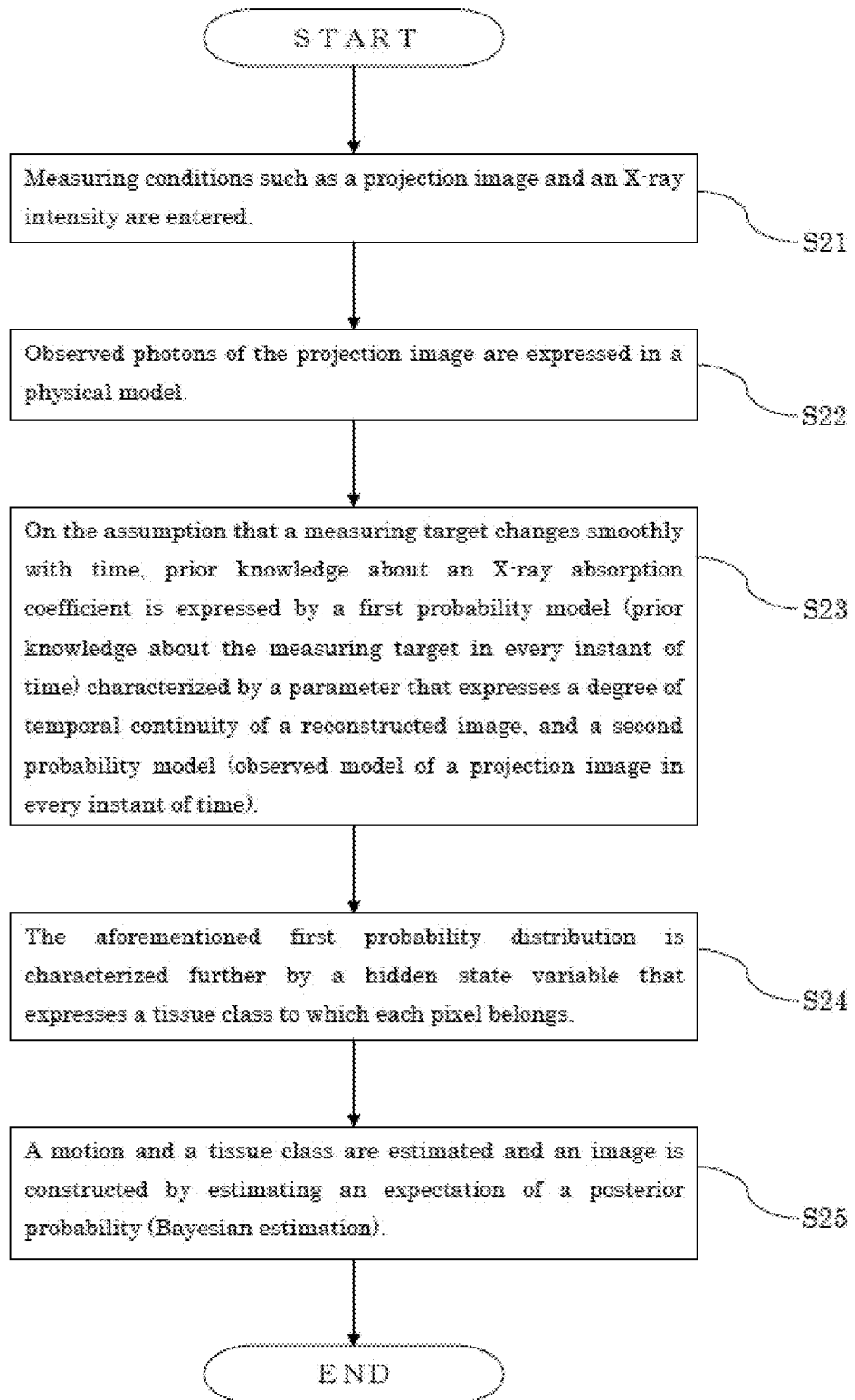
FIG. 4 shows a flow diagram (2) of a motion tracking X-ray CT image processing method of the present invention.

FIGS. 3 and 4 each show a flow of an embodiment of the motion tracking X-ray CT image processing method of the present invention.

As shown in the flow of FIG. 3, in one embodiment of the flow of the motion tracking X-ray CT image processing method of the present invention, measuring conditions such as a projection image and an X-ray intensity are entered (Step S11). Observed photons of the projection image are expressed in a physical model (Step S12). On the assumption that a measuring target changes smoothly with time, prior knowledge about X-ray absorption coefficients is expressed by a first probability model (prior knowledge about the measuring target in every instant of time) characterized by a parameter that expresses a degree of temporal continuity of a reconstructed image, and a second probability model (observed model of a projection image in every instant of time) (Step S13). A motion and a tissue class are estimated and an image is constructed by estimating an expectation of a posterior probability (Bayesian estimation) (Step S14).

As shown in the flow of FIG. 4, in a different embodiment of the flow of the motion tracking X-ray CT image processing method of the present invention, the aforementioned first probability distribution is characterized further by a hidden state variable that expresses a tissue class to which each pixel belongs (Step S24).

Image construction has an ill-posed problem. This is solved by imposing some limitation on a reconstructed image (X-ray absorption coefficient) as a solution using appropriate prior knowledge. This limitation includes temporal limitation to become a significant part of the present invention to be imposed on reconstructed images of neighboring frames. The measuring target is assumed to be deformed smoothly with time, so that reconstructed images of neighboring frames make motions responsive to the motion $m_j^{(k)}$ of each pixel j, as shown in FIG. 2. Accordingly, if the reconstructed image in the (k−1)-th frame is deformed according to the motion $m_j^{(k)}$ a resultant image should have strong temporal correlation with the reconstructed image in the k-th frame. This temporal limitation on a reconstructed image is expressed in the form of a probability distribution by both direct temporal correlation between reconstructed images and indirect temporal correlation described later determined through a substance or a tissue assumed to exist potentially behind a reconstructed image, or by either of these temporal correlations.

Figure 5:
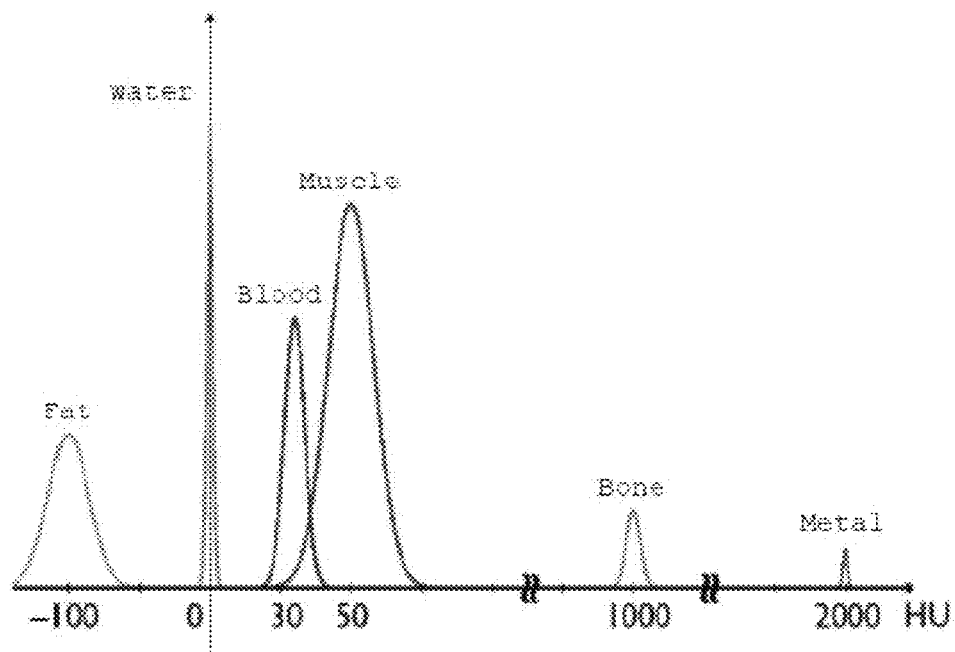
FIG. 5 shows a distribution diagram of X-ray absorption coefficient for each tissue class.

The following describes the limitation imposed through a substance or a tissue. As shown in FIG. 5, a human body is formed of limited substances and tissues such as fat, water, blood, muscle, bone and metal (such as implant). Each of these substances and tissues (hereinafter called tissues simply) can be characterized in the form of a probability distribution showing that each of these tissues is subjected to limitation as it is likely to take on a typical X-ray absorption coefficient. Deformation of a tissue in compliance with a motion of a measuring target can be expressed in the same way as that of expressing temporal correlation between reconstructed images of neighboring frames. This limitation can be characterized in the form of a probability distribution. Knowledge that each tissue has its spatial continuity and a ratio of each tissue to a human body is roughly known can be characterized further as limitation on the tissue in the form of a probability distribution.

Figure 6:
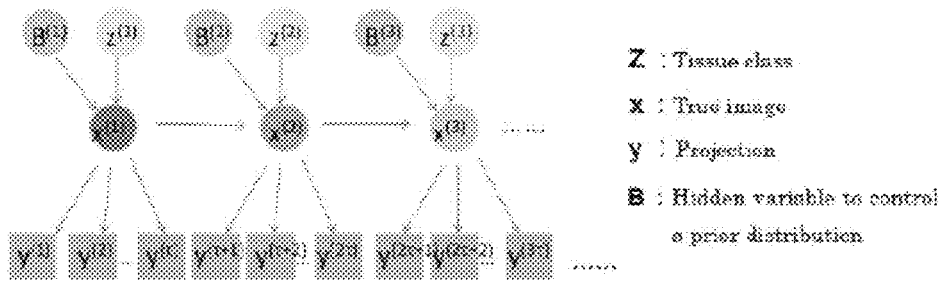
FIG. 6 shows an explanatory view showing dependence of probability variables in a CT probability model assuming a hidden state variable to control a motion, a tissue class, and a prior distribution of a tissue class.

FIG. 6 shows the particulars of FIG. 1(2) showing causal relationships between variables according to the probability model of the present invention. A scanning time is divided into frames of a significantly short temporal width and a target in each frame is expressed in the same CT image (in FIG. 6, this is expressed as $x^{(1)}$, $x^{(2)}$, ...). Some hundreds to some thousands of projections are obtained in a short time such as 0.3 seconds as a result of actual scanning. Accordingly, multiple projections y are obtained from one x in each frame. In response to the ill-posed problem, a tissue class Z is introduced. While Z is given, the X-ray absorption coefficient x is assumed to take on a value fixed to a certain degree. Further, B is a hidden state variable to control the shape of a prior distribution and is given to make the prior distribution more robust.

Figure 7:
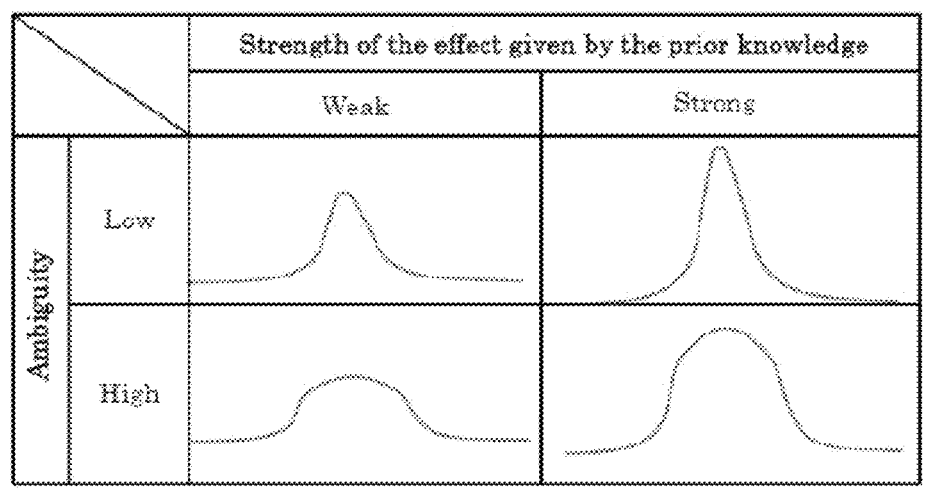
FIG. 7 shows an explanatory view showing an effect achieved by introducing the hidden state variable B.

FIG. 7 shows effect achieved by introducing the hidden state variable B. In the absence of the hidden state variable B to control the shape of a prior distribution, if vagueness is lowered by reducing the dispersion of the prior distribution, for example, the effect of prior knowledge is made stronger accordingly. The prior distribution can be expressed as a mixture distribution by introducing B, so that the vagueness of the prior knowledge and the strength of the effect can be controlled separately.

Then, statistical estimation is made based on a posterior distribution. An image can be reconstructed by determining a value that maximizes the posterior distribution about the reconstructed image (MAP estimation) or by determining an expectation (Bayesian estimation). Generally, the Bayesian estimation intended to determine the expectation of a posterior probability has higher resistance to disturbance. Meanwhile, calculation of the posterior probability involves integration calculation of a high-dimensional hidden state variable, so that making the calculation analytically becomes difficult. The difficulty in the calculation is overcome by applying an approximation technique of determining the posterior probability approximately. Regarding statistical estimation made by estimating the posterior distribution, the aforementioned difficulty in the calculation may alternatively be overcome by applying the MAP estimation that maximizes a joint posterior probability containing both a hidden state variable and a reconstructed image without making integration calculation of a hidden state variable.

(Formulation of Problem)

T projection data segments obtained from projections from various directions are called $D=\{Y^{\{1\}}, \ldots, Y^{\{T\}}\}$. Each of data segments $Y^{(t)}$ forms a set $Y^{\{t\}}=\{y_1^{\{t\}}, \ldots, y_I^{\{t\}}\}$ of data segments detected by a detector as a result of a t-th projection. Further, $y_i^{(t)}$ means the number of photons detected by an i-th detector. Where a sufficiently large number of projections are obtained in a short time, assuming that X-ray CT images obtained in this short time are the same can reduce a calculation amount as it can reduce X-ray CT images to be estimated. Then, each projection is divided into K frames and it is assumed that a projection image can be obtained from the same X-ray CT image in each frame. A set of indexes about projection data belonging to a k-th frame is called $S^{(k)}$ and an X-ray CT image in the k-th frame is called $X^{(k)}$. An X-ray is exponentially attenuated while it passes through a substance. Accordingly, an average $y_i^{(t)}$ or X-ray photons expected to be observed can be expressed by the following Equation 1.

[Equation 1]

$$\hat{y}_i^{(t)} = v\exp\left(-\sum_{j=1}^{J} l_{ij}^{(t)} x_j^{(k)}\right) \tag{1}$$

Where $t \in \hat{S}^{(k)}$

In the Equation 1, $x_j^{(k)}$ is the X-ray absorption coefficient of a j-th pixel of a J-dimensional vector $x=\{x_1, \ldots, x_J\}$ obtained by raster scanning the X-ray absorption coefficient of an imaging target in a k-th frame, v is the number of photons emitted from an X-ray source (the number of photons that can be observed in the absence of any object), $l_{ij}^{(t)}$ is proportionate to a crossover distance between a projection line projected at an angle $\theta^{(t)}$ and detected by the i-th detector and the j-th pixel, and $l_{ij}^{(t)} x_j$ is an effective X-ray absorption coefficient of a j-th pixel region regarding an X-ray corresponding to a t-th projection and entering the i-th detector.

The following describes a physical model relating to photons observed in a projection image, a prior distribution about a tissue functioning as prior knowledge, specifically a parameter distribution showing an existing ratio of each tissue of an imaging target, a parameter distribution showing a typical X-ray absorption coefficient each tissue is likely to take on, a parameter distribution showing a degree of spatial continuity of each tissue, and a parameter distribution showing a degree of temporal continuity of each tissue that are adopted in the motion tracking X-ray CT image processing method and the motion tracking X-ray CT image processing program of the present invention.

(Physical Model about Observed Photons)

In X-ray CT, shot noise of detected photons is considered to be a main cause for noise in observed data. Thus, observed data about photons is modeled on the assumption that the observed data is generated according to the Poisson distribution independent for each projection and for each detector.

The Poisson distribution is given not for particular limitation but a different physical model capable of showing physical process satisfactorily is also applicable.

The aforementioned Equation 1 shows an average of the Poisson distribution. The following Equation 2 is established using a result of the Equation 1. Noise is independent for each projection and for each pixel, so that the Equation 2 is expressed as the product of the entirely independent Poisson distributions. In the Equation 2, $S^{(k)}$ is a set of indexes of projections in the k-th frame.

[Equation 2]

$$p(D \mid X) = \prod_{k=1}^{K} \prod_{t \in S^{(k)}} \prod_{i=1}^{I} \frac{\hat{y}_i^{(t)} y_i^{(t)} e^{-\hat{y}_i^{(t)}}}{y_i^{(t)}!}. \quad (2)$$

(Prior Distribution about Motion)

Assuming that a distribution of a tissue class is expressed as the Boltzmann distribution while the motion θ is given, a prior distribution about the tissue class is modeled as shown in the following Equation 3. In the Equation 3, $A_1$ is a normalizing constant, and $H_1(Z)$ is an energy function showing which combination of tissue classes has a maximum likelihood. The energy function $H_1(Z)$ is expressed by the following Equation 4.

In the Equation 4, z is a vector showing a tissue class to which the j-th pixel belongs in the k-th frame. If the j-th pixel belongs to a tissue class c, $z_{jc}^{(k)}$ becomes 1 and the other components become 0. Here, $Z_j^{(k)} = [z_{j1}^{\{k\}}, \ldots, z_{jc}^{\{k\}}] \in \{0,1\}^c$ in uppercase means a set of variables $z_j^{(k)}$ where z is in lowercase.

[Equation 3]

$$p(Z \mid \theta) = \frac{1}{A_1} \exp\{-H_1(Z)\} \quad (3)$$

$$A_1 = \sum_Z \exp\{-H_1(Z)\}$$

[Equation 4]

$$H_1(Z) = -\sum_{c=1}^{C} \sum_{k=1}^{K} \sum_{j=1}^{J} \left\{ \begin{array}{l} G_c^{self} z_{jc}^{(k)} + \sum_{s \in \eta(j)} G_c^{inter} z_{jc}^{(k)} z_{sc}^{(k)} + \\ \sum_{i \in N(j)} G(i,j,m^{(k)}(\theta)) z_{jc}^{(k)} z_{ic}^{(k-1)} \end{array} \right\}. \quad (4)$$

In the aforementioned Equation 4, η(j) means four neighboring pixels of the j-th pixel, and (N)(j) means surrounding 9×9 (pixels) including the j-th pixel. In the Equation 4, the first term shows a ratio of a tissue, the second term shows spatial smoothness (continuity) of a tissue in the same frame, and the third term shows temporally smooth displacement or deformation of a tissue between neighboring frames. In the Equation 4, $G(i,j,m^{\{k\}}(\theta))$ is the weight of the third term of $H_1(Z)$ and is expressed by the following Equation 5. On the assumption that each pixel in the (k−1)-th frame makes a motion in neighboring frames ((k−1)-th and k-th frames) according to a current motion $m^{(k)}(\theta)$, a distance from each pixel in the k-th frame is calculated. The weight becomes larger with increase in this distance.

[Equation 5]

$$G(i, j, m^{(k)}(\theta)) = \frac{G_c^{time} \exp(-\gamma \|r_j - (r_i + m_i^{(k)}(\theta))\|)}{\sum_{i \in N(j)} \exp(-\gamma \|r_j - (r_i + m_i^{(k)}(\theta))\|)} \quad (5)$$

(Prior Distribution about Reconstructed Image X)

The following Equation 6 shows a prior distribution about a reconstructed image X. Given the tissue class Z and the hidden state variable B, X-ray absorption coefficients is expressed as the Gaussian distribution. As described below, an average of the Gaussian distribution is set for each tissue class. A degree of approximation to the value of X-ray absorption coefficients typical of each tissue class is controlled by a hidden state variable b. In each frame k and each pixel j, $b_{j1}^{(k)}$ and $b_{j2}^{(k)}$ are variables either of which takes on 1 and the other takes on 0. Values $v_{c1}$ and $v_{c2}$ of X-ray absorption coefficients given for each tissue class c and typical of this tissue class c are generally set to be equal: $v_{c1} = v_{c2}$. As an example, the value of an average $v_k$ is set as $v_1 = 0.000$, $V_2 = 0.018$, $V_3 = 0.022$, $V_4 = 0.040$, $V_5 = 0.120$ for each tissue (such as air, fat, muscle, bone or metal). Dispersion parameters $\epsilon_{c1}^2$ and $\epsilon_{c2}^2$ have values fixed for each tissue class c: one of the values takes on a large positive value and the other value takes on a small positive value. Further, $v_{c1}$, $v_{c2}$, $\epsilon_{c1}^2$ and $\epsilon_{c2}^2$ are obtained as a result of parameter study conducted manually by an expert or using ease of application to a large number of actually acquired projection images as a reference. The first term of the Equation 6 is to determine a degree of approximation of X-ray absorption coefficients given by a reconstructed image to the value of a typical X-ray absorption coefficient. Either of the hidden state variables $b_{j1}^{\{k\}}$ and $b_{j2}^{\{k\}}$ takes on 1 and the other takes on 0. Accordingly, a degree of approximation to the value of X-ray absorption coefficients typical of the tissue class c of a reconstructed image is determined not only by the tissue class c but is also controlled by the values of $b_{j1}^{\{k\}}$ and $b_{j2}^{\{k\}}$ for each frame k and each pixel j. In addition to the dispersion parameters $\epsilon_{c1}^2$ and $\epsilon_{c2}^2$ fixed for each tissue class c, the hidden state variables $b_{j1}^{\{k\}}$ and $b_{j2}^{\{k\}}$ estimated from a given projection image are prepared and used for estimation. This enables adaptive control of a degree of approximation for each frame and for each pixel, so that uncertainty about which X-ray absorption coefficient is to be employed easily by each tissue class and influence of the uncertainty can be controlled separately. The second and third terms of the Equation 6 respectively show that a reconstructed image changes spatially smoothly and that the reconstructed image is deformed temporally smoothly based on the motion vector m. Further, $G_x^{spatial}$ and $G_x^{temporal}$ are parameters used to control the strength of spatial correlation and the strength of temporal correlation respectively.

[Equation 6]

$$X = [x^{(1)}, \ldots, x^{(K)}] \quad Z = [z^{(1)}, \ldots, z^{(K)}] \quad B = [b^{(1)}, \ldots, b^{(K)}] \tag{6}$$

$$p(X \mid Z, B, \theta) = \frac{1}{A_0} \exp\left(-\frac{1}{2} E(X, Z, B, \theta)\right)$$

$$A_0 = \int \exp\left(-\frac{1}{2} E(X, Z, B, \theta)\right) dx^{(1)} \ldots dx^{(K)}$$

$$E(X, Z, B, \theta) =$$

$$\sum_{k=1}^{K} \sum_{j=1}^{J} \sum_{c=1}^{C} \left( \frac{b_{j1}^{(k)} z_{jt}^{(k)}}{2\varepsilon_{c1}^{1}} \left(x_{j}^{(k)} - v_{c1}\right)^2 + \frac{b_{j2}^{(k)} z_{jt}^{(k)}}{2\varepsilon_{c2}^{2}} \left(x_{j}^{(k)} - v_{c2}\right)^2 \right) +$$

$$\sum_{k=1}^{K} \sum_{j=1}^{J} \sum_{z \in \eta(j')} G_{x}^{spatial} \left(x_{j}^{(k)} - x_{i}^{(k)}\right)^2 +$$

$$G_{x}^{temporal} \sum_{k=2}^{K} \sum_{j=1}^{J} \left( x_{j}^{(k)} - \sum_{l \in N(j)} G(i, j, m^{(k)}(\theta)) x_{i}^{(k-1)} \right)^2$$

On the assumption that the hidden state variable B complies with the Boltzmann distribution (Equation 7 given below), an energy function $H_2(B)$ showing a combination of the hidden state variables B of a maximum likelihood is expressed by the following Equation 8. The first term of the Equation 8 shows which one of two values is to be taken on more easily by a set B of binary hidden variables, and the second term of the Equation 8 is to control spatial smoothness of a distribution (showing how easy for neighboring pixels to take on the same distribution).

[Equation 7]

$$p(B) = \frac{1}{A_2} \exp\{-H_2(B)\}, \tag{7}$$

[Equation 8]

$$H_2(B) = -\sum_{d=1}^{2} \sum_{k=1}^{K} \sum_{j=1}^{J} \left( G_d'^{self} b_{jd}^{(k)} + G_d'^{inter} \sum_{s \in \eta(j)} b_{jd}^{(k)} b_{sd}^{(k)} \right) \tag{8}$$

Further, $m_j^{(k)}(\theta)$ showing the motion of the j-th pixel from the (k−1)-th frame to the k-th frame is expressed by the following Equation 9. The Equation 9 is intended to determine the motion vector $m_j^{(k)}(\theta)$ of the j-th pixel in the k-th frame from a minority representative motion vector $\theta_i^{\{l\}}$ (i=1, ..., J, l=1, ..., K) by interpolation. This gives a heavier weight to a spatially and temporally approximate representative motion vector $\theta_i^{\{l\}}$ (i=1, ..., J, l=1, ..., K). In the Equation 9, $r_i$ is the position vector of an i-th pixel.

[Equation 9]

$$m_j^{(k)}(\theta) = \frac{\sum_{i,l} \exp(-\alpha \|r_i - r_j\| - \beta |k - l|) \theta_i^{(l)}}{\sum_{i,l} \exp(-\alpha \|r_i - r_j\| - \beta |k - l|)} \tag{9}$$

(Bayesian Estimation of Posterior Distribution)

Regarding a CT image reconstruction, the X-ray absorption coefficient x, the tissue class z, and the hidden state variable b are estimated as a posterior distribution p(X,Z,B|D, θ) of the observed data D and the motion θ of a measuring target. The posterior distribution p (X,Z,B|D,θ) can be understood from the Bayes' theorem and is obtained in proportion to the product of a corresponding prior distribution and a likelihood as shown by the following Equation 10. In the MAP estimation, obtaining the maximum of the posterior distribution p (X,Z,B|D,θ) eliminates the need for making calculation to obtain a sum of high-dimensional hidden state variables.

[Equation 10]

$$p(X,Z,B|D,\theta) \propto p(D|X) p(X|Z,B) p(Z|\theta) p(B) \tag{10}$$

The Bayesian estimation (approximate Bayesian estimation) evaluates the posterior distribution p having difficulty in calculation with a test distribution q(X,Z,B) approximate to the posterior distribution p(X,Z,B|D,θ). The Bayesian estimation itself is a method of calculating a posterior distribution and using the expectation thereof as an estimate value. A test distribution is not required if a posterior distribution and the expectation thereof can be calculated analytically. The test distribution q(X,Z,B) is determined so as to minimize an index called a KL distance indicating approximation of a distribution. The KL distance mentioned herein is defined by the following Equation 11.

[Equation 11]

$$D_{KL} = \left\langle \log \frac{p(X, Z, B \mid D, \theta)}{q(X, Z, B)} \right\rangle_{q(X,Z,B)} \tag{11}$$

In the Equation 11, $\langle \cdot \rangle_{q(X,Z,B)}$ is an operator showing integration calculation made on the test distribution q(X,Z,B), meaning that the expectation of the test distribution q(X,Z,B) is to be given. The distance KL is always non-negative and becomes 0 (zero) only if q=p is satisfied. To deal with difficulty in calculating a posterior distribution, a set of distributions that can be calculated is searched for to find a distribution most approximate to the posterior distribution.

The test distribution q(X,Z,B) can be selected in anyway such that the selected test distribution q(X,Z,B) allows minimization of the KL distance (aforementioned Equation 11) or minimization of approximation. Accordingly, for simple calculation, the test distribution q(X,Z,B) is given assumption of independence among the variables x, z and b called factored assumption as shown by the following Equation 12. Specifically, it is assumed that X, Z and B are independent of each other and are also independent for each frame and for each pixel. On the assumption that a distribution $q(x_j)$ about $x_j$ becomes the Gaussian distribution, the test distribution q is modeled as shown by the following Equation 13. Under the foregoing assumptions, alternate optimization of optimizing q(X), q(Z) and q(B) alternately is conducted to obtain an optimum test distribution.

[Equation 12]

$$q(X, Z, B) = \prod_{k=1}^{K} \prod_{j=1}^{J} q(x_j^{(k)}) q(z_j^{(k)}) q(b_j^{(k)}) \tag{12}$$

[Equation 13]

$$q(x_j^{(k)}) \sim N(x_j^{(k)} \mid \mu_j^{(k)}, \sigma_j^{(k)2}) \tag{13}$$

An analytical solution is obtained if q(X) and q(B) are fixed to currently obtained estimate values and only q(Z) is optimized so as to allow minimization of $D_{KL}$ in the aforementioned Equation 11. Likewise, an analytical solution is obtained if q(X) and q(Z) are fixed to currently obtained estimate values and only q(B) is optimized so as to allow minimization of $D_{KL}$ in the aforementioned Equation 11.

Even if q(Z) and q(B) are fixed to currently obtained estimate values, an analytical solution cannot be obtained from q(X). In this case, the parameters μ and σ of q(X) in the aforementioned Equation 13 are obtained by numerical optimization. These distributions q(X), q(Z) and q(B) are subjected to optimization until a predetermined convergence condition is satisfied to obtain a solution.

The substance of the motion tracking X-ray CT image processing method and that of the motion tracking X-ray CT image processing program of the present invention have been described above. In examples given below, an object to be deformed was formed artificially, a screen was reconstructed from a projection image of the object, and this screen reconstruction was evaluated by being compared to screen reconstruction of prior art. Evaluation experiments given below are believed to contribute to deeper understanding of the usefulness of the motion tracking X-ray CT image processing method and the motion tracking X-ray CT image processing program of the present invention.

[Embodiment 1]

In Example 1, an object to be deformed was formed artificially and a screen was reconstructed based on a projection image of the object by calculator simulation using the motion tracking X-ray CT image processing method of the present invention. A result of the simulation is given below.

Figure 8:
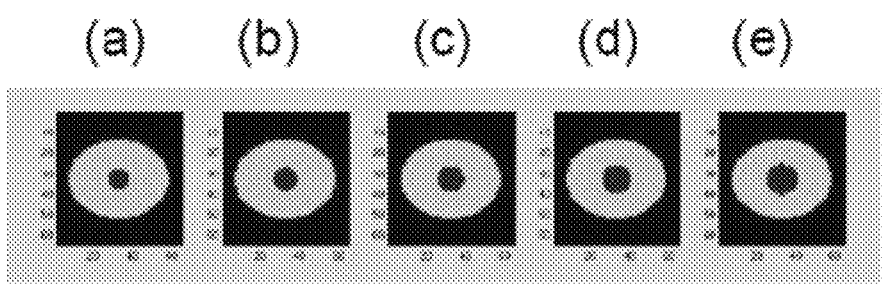
FIG. 8 shows an explanatory view showing an object to be deformed over time.

Images in FIG. 8 show an artificially formed image to be deformed. As shown in FIG. 8, a central area of each round screen shows the object (64×64 pixels). The object expanded from (a) to (e) with time. The deformation of the object is such that the object expanded at a rate differing between the vertical and horizontal directions.

Figure 9:
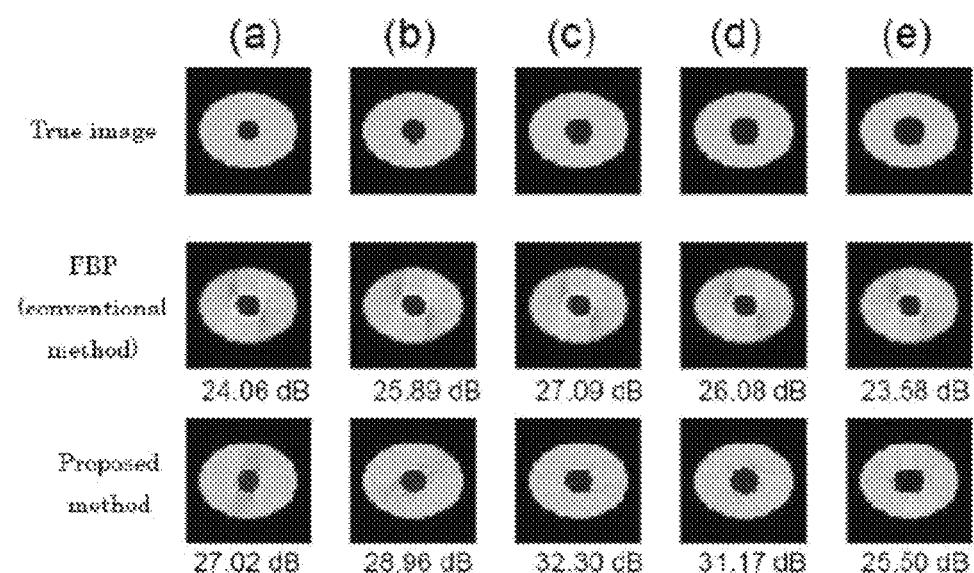
FIG. 9 shows an explanatory view showing results of reconstruction of CT images relative to an object to be deformed over time.

FIG. 9 shows results of reconstruction of X-ray CT images. FIG. 9 is given to compare true images, results of image reconstruction obtained by a filtered back projection (FBP) method employed most frequently as a conventional method not assuming a motion, and results obtained by the image reconstruction of the present invention (suggested method).

Differences between the reconstructed images obtained by each of these methods and the true images were evaluated in terms of PSNR (Peak signal to noise ratio). Here, PSNR is defined by the following Equation 14.

[Equation 14]

$$PSNR = 10\log_{10}\frac{\max_i y_i}{MSE} \quad (14)$$

In the aforementioned Equation 14, MSE is a mean squared error between pixel values of the true images and those of the reconstructed images, and $\max_i y_i$ is the maximum pixel value of the true images. The value of PSNR is given below each image of FIG. 9.

The results of FIG. 9 show that the present invention achieves enhancement of about 3.8 (dB) on average in terms of PSNR. The enhancement of about 3.8 (dB) corresponds to an error reduction of about 42% in terms of the mean squared error. The resultant images further show that the motion of the object in the center of these images can be expressed satisfactorily.

Figure 10:
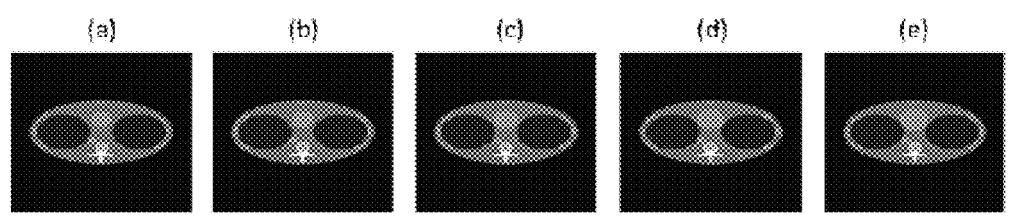
FIG. 10 shows an explanatory view showing a chest model involving the motion of a heart.

FIG. 10 shows images about a chest model involving the motion of a heart. These images are given to simulate a chest involving the motion of a heart. As shown in FIG. 10, an ellipse corresponding to the heart above the center expanded such that the ellipse increased gradually, specifically such that the ellipse expanded from (a) to (e) with time. The deformation of the ellipse is such that the ellipse expanded at a rate differing between the vertical and horizontal directions. The image size of the chest model was 256×256 (pixels) and the number of projections was 360 within 360 degrees.

Figure 11:
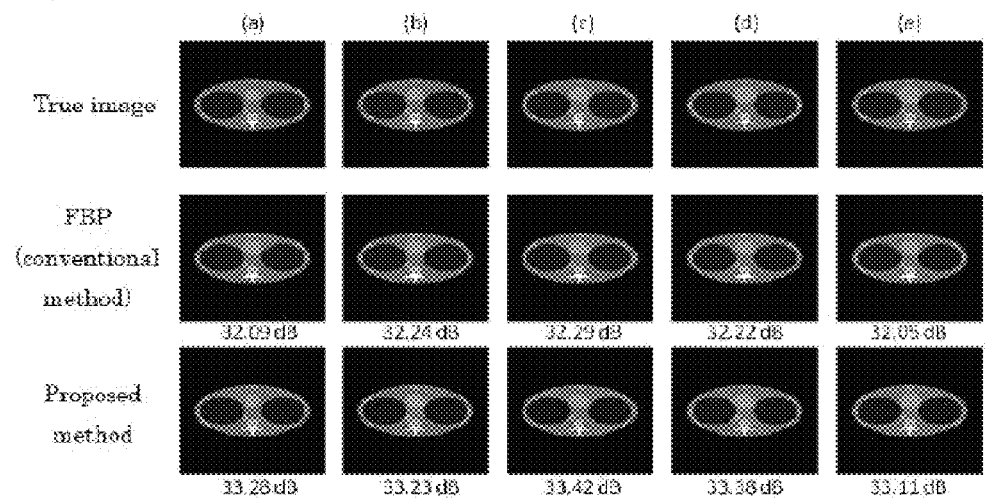
FIG. 11 shows an explanatory view showing results of reconstruction of CT images relative to a chest model involving the motion of a heart.

FIG. 11 shows results of reconstruction of X-ray CT images. FIG. 11 is given to compare true images, results of image reconstruction obtained by a filtered back projection (FBP) method employed most frequently as a conventional method not assuming a motion, and results obtained by the image reconstruction of the present invention (suggested method).

The results of FIG. 11 show that the present invention achieves enhancement of about 1.1 (dB) on average in terms of PSNR. The enhancement of about 1.1 (dB) corresponds to an error reduction of about 22% in terms of the mean squared error. The resultant images also show that the motion of the heart can be expressed satisfactorily.

[Embodiment 2]

The motion tracking X-ray CT image processing method of the present invention uses a probability model that makes statistical estimation as described above, so that it can incorporate other prior knowledge easily and can increase the quality of image reconstruction. As an example, making estimation in consideration of X-ray absorption coefficients representative of each tissue can enhance estimation accuracy. In this case, incorporating a hidden state variable to control the distribution of each tissue class can enhance estimation accuracy and can achieve robust estimation. The following describes experiment conducted to check the effect thereof.

Figure 12:
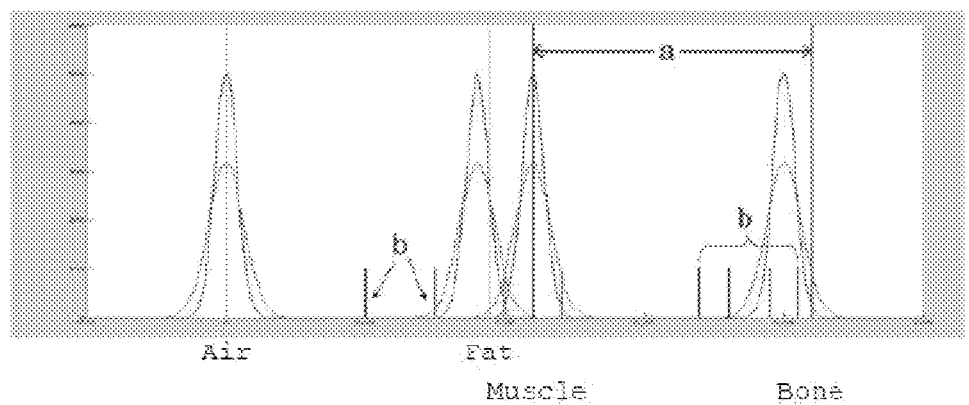
FIG. 12 shows an effect achieved by introducing the hidden state variable b that controls a distribution of tissue class.

FIG. 12 shows the X-ray absorption coefficient of an assumed tissue class and the value of the X-ray absorption coefficient of an object actually used in experiment. Here, it is assumed that there are four tissue classes including air, fat, muscle and bone, and that there is X-ray absorption coefficients representative of each tissue class.

In consideration of a shift of the value of the X-ray absorption coefficient from an assumed representative value, during actual projection, the X-ray absorption coefficient of each of the fat class and the bone class was made higher by 10% as indicated by lines with sign a in FIG. 12. Lines with sign b in FIG. 12 show other outliers of X-ray absorption coefficients. X-ray CT was conducted on an object taking on a value higher by 5% than an assumed representative X-ray absorption coefficient about fat and muscle belonging to the aforementioned tissue classes.

Figure 13:
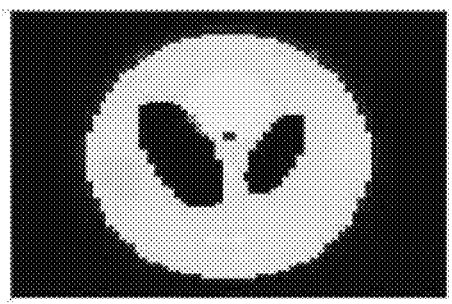
FIG. 13 shows results of reconstruction of CT images.
Figure 13:
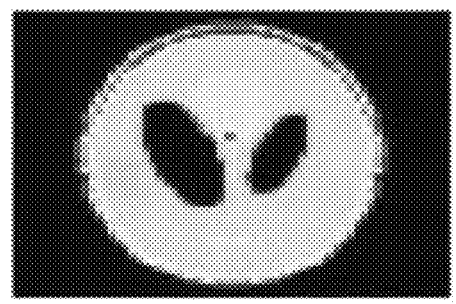
Figure 13:
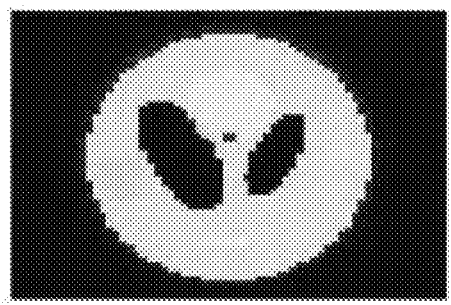
Figure 13:
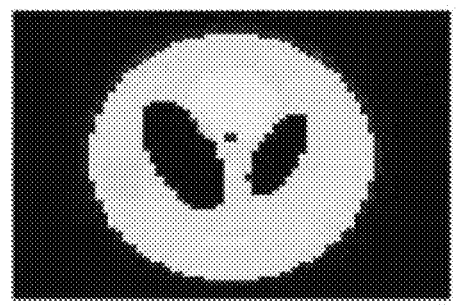
Figure 13:
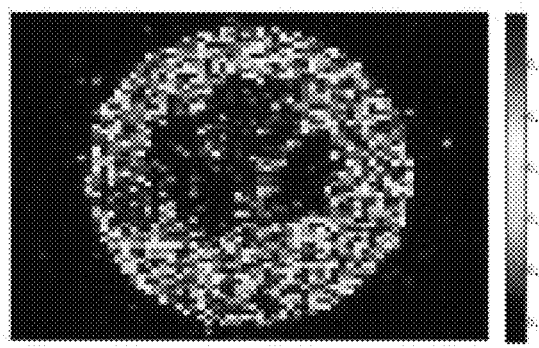
Figure 14:
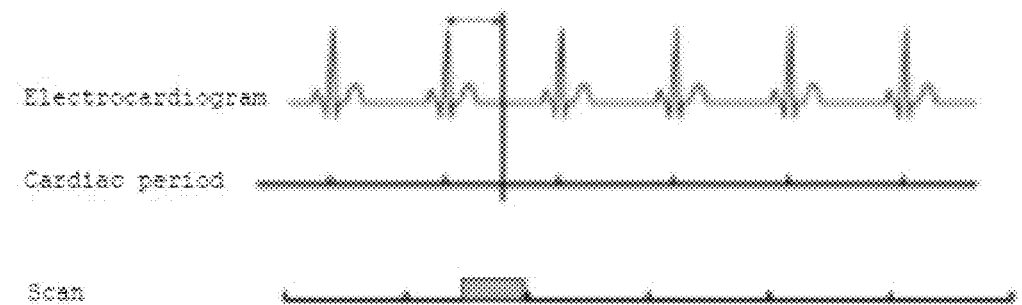
FIG. 14 shows an explanatory view showing prior-art 1.
Figure 15:
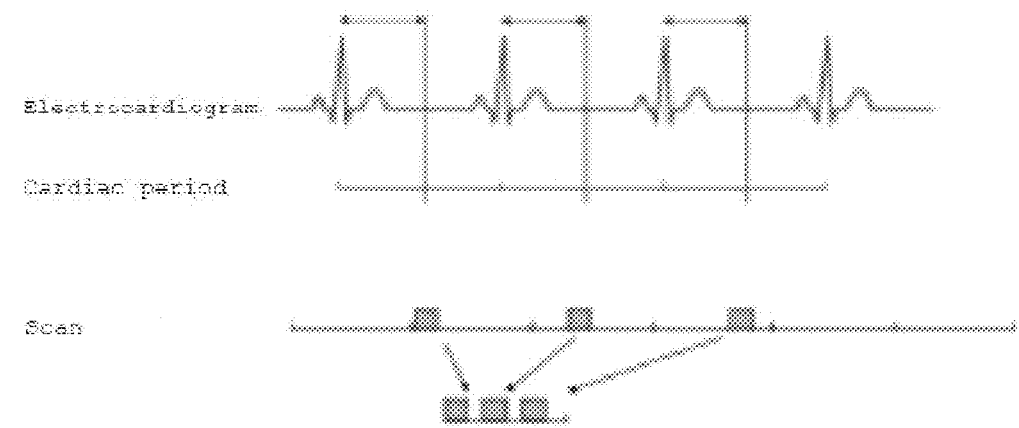
FIG. 15 shows an explanatory view showing prior-art 2.

FIG. 13 is given to compare results of X-ray CT reconstructions given under the aforementioned condition setting. In FIG. 13, (1) shows a true image, (2) shows an image reconstructed by FBP, (3) shows an image reconstructed by the present invention in the absence of introduction of the hidden state variable B, (4) shows an image reconstructed by the present invention in the presence of introduction of the hidden state variable B, and (5) shows the estimated hidden state variable B.

The presence and the absence of introduction of the hidden state variable B achieved enhancement of 0.8 (dB) in terms of PSNR (enhancement of about 17% in terms of the mean squared error). In comparison to the conventional filtered back projection (FBP) method, enhancement of 17.6 (dB) is achieved. Further, an assumed shift of the X-ray absorption coefficient of each tissue from an assumption was a small shift of only 5%. Accordingly, a larger effect is expected to be achieved on the occurrence of a larger shift.

The foregoing results were obtained with a relatively simple probability model. While estimation accuracy has room for enhancement, the estimation accuracy itself is considered to reach a level sufficient for practical use. An optimum parameter for practical use is to be determined depending on actual specifications of a measuring unit or the characteristics of a measuring target. Thus, knowing the actual specifications of the measuring unit or the characteristics of the measuring target is necessary for determining the optimum parameter.

[Embodiment 3]

In Example 3, an X-ray CT algorithm is described different from that of Examples 1 and 2 described above.

(1) Probability Model (1-a) Likelihood

ACT image of an object targeted for reconstruction is expressed by an one-dimensional vector $X=[x_1, \ldots, x_J]$ (J is the number of pixels of a reconstructed image). Projection mentioned herein is to be made on an object to be deformed or to move with time. Accordingly, time is divided into K frames $S^{\{k\}}$, $k \in \{1, \ldots, K\}$ and a CT image in a k-th frame is expressed as $X^{\{k\}}=[x_1^{\{k\}}, \ldots, x_J^{\{k\}}]$. CT images $X^{\{k\}}$ ($k \in \{1, \ldots, K\}$) in all the frames are expressed collectively as $X=\{X^{\{1\}}, \ldots, X^{\{K\}}\}$.

An image obtained by projection on the object at a time t is expressed as $Y^{\{t\}}=[y_1^{\{t\}}, \ldots, y_I^{\{t\}}]$ (I is the number of detectors) and projections in all instants of time are expressed collectively as $D=\{Y^{\{1\}}, \ldots, Y^{\{T\}}\}$. It is assumed that projection of a CT image $X^{(k)}$ is obtained if the time t satisfies $t \in S^{(k)}$. The following Equations 15 and 16 can be established in consideration of the situation where noise caused by photoelectric conversion complies with an independent Poisson distribution.

[Equation 15]

$$p(D|X) = \prod_k \prod_{i \in S^{(k)}} \prod_i p(y_i^{(t)}|X^{(k)}) \quad (15)$$

[Equation 16]

$$p(y_i^{(t)}|X^{(k)}) = \frac{\hat{y}_i^{(t)y_i^{(t)}} \exp(-\hat{y}_i^{(t)})}{y_i^{(t)}!} \quad (16)$$

where $$\hat{y}_i^{(t)} = b \exp(-L^{(t)} X^{(k)}) \ (t \in S^{(k)})$$

In the aforementioned Equation (16), $L^{(t)}$ is a matrix of m×n, and the element (i,j) indicates a degree of intersection of a beam of an emitted X-ray to enter a detector i with a pixel j of a reconstructed image. In the aforementioned Equation (16), b is the number of photons (the number of emitted photons) during blank scanning. Here, the Gaussian distribution is applicable as a noise distribution.

(1-b) Prior Distribution

A prior distribution is expressed by the following Equation 17.

[Equation 17]

$$p(X|\theta) = \sum_Z \sum_B p(X, Z, B|\theta) \quad (17)$$

In the Equation 17, Z and B are each composed of a variable corresponding to each pixel of a CT image: Z is a variable $Z=\{Z^{\{1\}}, \ldots, Z^{\{K\}}\}$ indicating a tissue class and B is a variable $B=\{B^{\{1\}}, \ldots, B^{\{K\}}\}$ to control a distribution shape. Variables to control a tissue class and a distribution shape in a k-th frame are expressed as $Z^{(k)}=[z_1^{\{k\}}, \ldots, z_J^{\{k\}}]$ and $B^{(k)}=[b_1^{\{k\}}, \ldots, b_J^{k}]$ respectively. Given the number of tissue classes to be assumed is C, a tissue class of each pixel is expressed by a C-dimensional vector $z_j^{\{k\}}=[z_{j1}^{\{k\}}, \ldots, z_{jC}^{\{k\}}]$. The element $z_{jC}(k)$ becomes 1 only if it is applied to the tissue class c to which the pixel j in the k-th frame belongs whereas the other elements become zero. Accordingly, the limitation in the following Equation 18 is satisfied. The variable $b_j^{(k)}$ to control the distribution shape of the pixel j in the k-th frame is a two-dimensional vector shown in the following Equation 19. A more complicated distribution can be expressed by increasing the number of values that can be taken on by d to any value higher than 2.

[Equation 18]

$$z_{jc} \in \{0,1\}, \Sigma_{c=1}^{C} z_{jc} = 1 \quad (18)$$

[Equation 19]

$$b_j^{(k)} = [b_{j1}^{(k)}, b_{j2}^{(k)}]^T, b_{jd}^{(k)} \in \{0,1\} (d=1,2), \Sigma_{d=1}^{2} b_{jd} = 1 \quad (19)$$

A parameter θ is defined as a parameter indicating a motion. A prior distribution is expressed by the following Equation 20.

The Equation 20 includes E(X,Z,B,θ) that is expressed by the following Equation 21.

[Equation 20]

$$p(X, Z, B|\theta) = \frac{1}{A_0} \exp\left(-\frac{1}{2} E(X, Z, B, \theta)\right) \quad (20)$$

where $$A_0 = \sum_Z \sum_W \int \exp\left(-\frac{1}{2} E(X, Z, B, \theta)\right) dX$$

-continued

[Equation 21]

$$E(X, Z, B \mid \theta) = \sum_{k=1}^{K} \sum_{j=1}^{J} \sum_{c=1}^{C} z_{jc}^{(k)} \left( \frac{b_{j1}^{(k)}}{2e_{c1}^2} \left(x_j^{(k)} - v_{c1}\right)^2 + \frac{b_{j2}^{(k)}}{2e_{c2}^2} \left(x_j^{(k)} - v_{c2}\right)^2 \right) +$$
$$\sum_{k=1}^{K} \sum_{j=1}^{J} \sum_{s \in \eta(j)} \left( \sum_{c=1}^{C} \sum_{c'=1}^{C} \sum_{d=1}^{2} \sum_{d'=1}^{2} G_{x,cd}^{spatial} z_{jc}^{(k)} z_{sc'}^{(k)} b_{jd}^{(k)} b_{sd'}^{(k)} \right)$$
$$\left(x_j^{(k)} - x_s^{(k)}\right)^2 +$$
$$\sum_{k=1}^{K} \sum_{j=1}^{J} \sum_{s \in \eta(j)} \left( \sum_{c=1}^{C} \sum_{c'=1}^{C} G_{x,c}^{spatial} z_{jc}^{(k)} z_{sc'}^{(k)} \right) \left(x_j^{(k)} - x_s^{(k)}\right)^2 +$$
$$G_x^{temporal} \sum_{k=2}^{K} \sum_{j=1}^{J} \left( x_j^{(k)} - \sum_{i \in N(j)} G(i, j, m^{(k)}(\theta)) x_i^{(k-1)} \right)^2 -$$
$$\sum_{k=1}^{K} \sum_{j=1}^{J} \sum_{c} \sum_{d} G_{cd}^{self} z_{jc}^{(k)} b_{jd}^{(k)} -$$
$$\sum_{k=1}^{K} \sum_{j=1}^{J} \sum_{s \in \eta(j)} \sum_{c=1}^{C} G_{zc}^{spatial} z_{jc}^{(k)} z_{sc}^{(k)} -$$
$$\sum_{k=1}^{K} \sum_{j=1}^{J} \sum_{s \in \eta} \sum_{c=1}^{C} \sum_{d=1}^{2} G_{b,cd}^{spatial} z_{jc}^{(k)} z_{sc}^{(k)} b_{jd}^{(k)} b_{sd}^{(k)} +$$
$$G_z^{temporal} \sum_{k=2}^{K} \sum_{j=1}^{J} \sum_{c=1}^{C} z_{jc}^{(k)} \sum_{i \in N(j)} G(i, j, m^{(k)}(\theta)) z_{ic}^{(k-1)}$$

Parameters and Variables are Described Next.

A parameter expressed by the following Equation 22 takes on a value $G_{x,cd}^{spatial}$ only if $z_{jc}^{\{k\}} = z_{sc'}^{\{k\}} = b_{jd}^{\{k\}} = b_{sd'}^{\{k\}} = 1$ is satisfied. A parameter expressed by the following Equation 23 takes on the value $G_{x,c}^{spatial}$ only if $z_{jc}^{\{k\}} = z_{sc'}^{\{k\}} = 1$ is satisfied.

[Equation 22]

$$\sum_{c=1}^{C} \sum_{c'=1}^{C} \sum_{d=1}^{2} \sum_{d'=1}^{2} G_{x,cd}^{spatial} z_{jc}^{(k)} z_{sc'}^{(k)} b_{jd}^{(k)} b_{sd'}^{(k)} \quad (22)$$

[Equation 23]

$$\sum_{c=1}^{C} \sum_{c'=1}^{C} G_{x,c}^{spatial} z_{jc}^{(k)} z_{sc'}^{(k)} \quad (23)$$

Accordingly, changing $G_{x,cd}^{spatial}$ can control a level of smoothness the pixel value x should acquire if neighboring pixels are in the same tissue class and have the same distribution shape control variable. Changing $G_{x,c}^{spatial}$ can also control a level of smoothness the pixel value x should acquire if neighboring pixels are in the same tissue class without depending on their distribution shape control variables. Likewise, $G_{z,c}^{spatial}$ controls how likely neighboring pixels are in the same tissue class. If the neighboring pixels are in the same tissue class, $G_{b,cd}^{spatial}$ further controls the similarity of distribution shape control variables of the neighboring pixels. Additionally, $G_{cd}^{self}$ indicates a combination of tissue class variables and distribution shape control variables that is to be generated easily. Variables $G_x^{temporal}$ and $G_z^{temporal}$ are to respectively control how easily variables x and z makes time transitions in compliance with the motion parameter θ. Further, η(j) and N(j) each show a set of pixel indexes near the pixel j. Each of η(j) and N(j) is to determine a range of smoothness and preferably, should be small for saving of a calculation amount.

The function $G(I,j,m^{\{k\}},(\theta))$ is defined by the following Equation 24. In the Equation 24, $r_i$ is the position vector of a pixel i, $m_i^{(k)}(\theta)$ is a motion vector indicating the amount of movement of the pixel i from a frame k to a frame k+1. Specifically, the motion vector $m_i^{(k)}(\theta)$ indicates that the pixel i in the k-th frame is expected to move from a position $r_i$ to a position $r_i + m_i^{(k)}(\theta)$ in the (k+1)-th frame. Additionally, y is a given positive constant. Thus, the function $G(I,j,m^{\{k\}},(\theta))$ acts as a weighting function to take on a larger value for a pixel of an movement amount more approximate to an expected amount.

[Equation 24]

$$G(i, j, m^{(k)}(\theta)) = \frac{\exp(-\gamma \| r_j - (r_i + m_i^{(k)}(\theta)) \|)}{\sum_{j' \in N(i)} \exp(-\gamma \| r_{j'} - (r_i + m_i^{(k)}(\theta)) \|)} \quad \text{if } j \in N(i) \quad (24)$$

$$G(i, j, m^{(k)}(\theta)) = 0 \quad \text{otherwise}$$

The amount of movement is expressed by the motion vector $m_i^{(k)}$ defined by the following Equation 25. Regarding $\exp(-\alpha \| r_i - r_j \| - \beta |k-1|)$ as a temporal-spatial weight, the Equation 25 shows that a motion vector $m_i^{(k)}$ can be obtained by interpolation with the parameter $\theta_i^{(1)}$. Parameters α and β are to control the strength of spatial interpolation and that of temporal interpolation respectively.

[Equation 25]

$$m_j^{(k)}(\theta) = \frac{\sum_{i,j} \exp(-\alpha \| r_i - r_j \| - \beta |k - l|) \theta_i^{(l)}}{\sum_{i,j} \exp(-\alpha \| r_i - r_j \| - \beta |k - l|)} \quad (25)$$

If $G_{x,cd}^{spatial} = G_{x,c}^{spatial} = G_x^{temporal} = 0$ is satisfied, the following Equation 26 is expressed as a conditional independent expression on condition that P(X|Z,B,θ) should be independent while Z and B are given, as shown by the following Equation 27. In this case, P(X|Z,B,θ) can be expressed by the following Equation 28 formulated by varying the Equation 27.

[Equation 26]

$$p(X, Z, B \mid \theta) = \frac{1}{A_0} \exp\left(-\frac{1}{2} E(X, Z, B, \theta)\right) \quad (26)$$

[Equation 27]

$$p(X, Z, B \mid \theta) = \frac{1}{A_0} p(X \mid Z, B, \theta) p(Z, B \mid \theta) = \quad (27)$$

$$\frac{1}{A_0} \prod_{k=1}^{K} \prod_{j=1}^{J} p(x_j^{(k)} \mid z_j^{(k)}, b_j^{(k)}, \theta) p(Z, B \mid \theta)$$

-continued

[Equation 28]

$$p(X, Z, B \mid \theta) = p(x_j^{(k)} \mid z_{jc}^{(k)} = 1, b_{jd}^{(k)} = 1, \theta) = N(x_j^{(k)}; v_{cd}, \varepsilon_{cd}^2) \quad (28)$$

The aforementioned Equation 27 includes p(Z,B|θ) defined by the following Equation 29. The aforementioned Equation 26 includes E(X,Z,B,θ) defined by the following Equation 30. These definitions can reduce parameters to be set.

[Equation 29]

$$p(Z, B \mid \theta) = \frac{1}{A_0} \exp\left(-\frac{1}{2} E(Z, B, \theta)\right) \quad (29)$$

[Equation 30]

$$E(X, Z, B, \theta) = \quad (30)$$

$$-\sum_{k=1}^{K}\sum_{j=1}^{J}\sum_{c}\sum_{d} G_{cd}^{self} z_{jc}^{(k)} b_{jd}^{(k)} - \sum_{k=1}^{K}\sum_{j=1}^{J}\sum_{s \in \eta(j)}\sum_{c=1}^{C} G_{zc}^{spatial} z_{jc}^{(k)} z_{sc}^{(k)} -$$

$$\sum_{k=1}^{K}\sum_{j=1}^{J}\sum_{s \in \eta}\sum_{c=1}^{C}\sum_{d=1}^{2} G_{b,cd}^{spatial} z_{jc}^{(k)} z_{sc}^{(k)} b_{jd}^{(k)} b_{sd}^{(k)} +$$

$$G_{z}^{temporal} \sum_{k=2}^{K}\sum_{j=1}^{J}\sum_{c=1}^{C} z_{jc}^{(k)} \sum_{i \in N(j)} G(i, j, m^{(k)}(\theta)) z_{ic}^{(k-1)}$$

In consideration of the situation where the CT value x takes on a non-negative value, the gamma distribution can be used for $P(x_j^{\{k\}} \mid z_{jc}^{\{k\}}=1, b_{jd}^{\{k\}}=1, \theta)$. In this case, $P(x_j^{\{k\}} \mid z_{jc}^{\{k\}}=1, b_{jd}^{\{k\}}=1, \theta)$ is expressed by the following Equation 31. The Equation 31 includes $u_{cd}$ and $v_{cd}$ each functioning as a parameter of the gamma distribution.

[Equation 31]

$$p(x_j^{(k)} \mid z_{jc}^{(k)} = 1, b_{jd}^{(k)} = 1, \theta) = (x_j^{(k)})^{u_{cd}-1} \frac{\exp(-x_j^{(k)} / v_{cd})}{\Gamma(u_{cd}) v_{cd}^{u_{cd}}} \quad (31)$$

The following describes a method that estimates the CT image X, the tissue class variable Z, and the distribution shape control variable B while estimating the motion parameter θ using the aforementioned probability model.

(2) Estimation Method Based on Free Energy Minimization

For simple description, a general issue of estimating a hidden variable x from an observation variable y is considered. This issue can be related to the aforementioned probability model by regarding the observation variable as D and the hidden variable as X, Z and B. Free energy F is defined by the following Equation 32. The Equation 32 includes a distribution q (x) called a test distribution.

[Equation 32]

$$F(q(x),\theta) = -\int q(x) \log p(x,y|\theta) dx + \int q(x) \log q(x) dx \quad (32)$$

A log-likelihood log p(y|θ) can be expressed by the following Equation 33 using the free energy F. The Equation 33 includes a function KL[q(x)|p(x)] that is defined by Equation 34 if x is a real number. If x is a discrete variable, the function KL is expressed by Equation 35 and is used as a scale for measuring approximation of probability distributions. The function KL always takes on a negative value and becomes zero only if q(x)=p(x) is established.

[Equation 33]

$$\log p(y \mid \theta) = \int q(x) \log p(x, y \mid \theta) dx - \int q(x) \log p(x \mid y, \theta) dx = \quad (33)$$

$$\int q(x) \log p(x, y \mid \theta) dx - \int q(x) \log q(x \mid y, \theta) dx +$$

$$\int q(x) \log q(x) dx - \int q(x) \log p(x \mid y, \theta) dx =$$

$$-F(q(x), \theta) + KL[q(x) \mid p(x \mid y, \theta)]$$

[Equation 34]

$$KL[q(x) \mid p(x)] = \int q(x) \log \frac{q(x)}{p(x)} dx \quad (34)$$

[Equation 35]

$$KL[q(x) \mid p(x)] = \sum_{x} q(x) \log \frac{q(x)}{p(x)} \quad (35)$$

Maximum likelihood estimation is used frequently in parameter estimation. The maximum likelihood estimation is intended to optimize the following Equation 36. As seen from the aforementioned expression variation, a log-likelihood can be expressed by the following Equation 37 using free energy. The left side of the Equation 37 shows an amount that does not depend on the test distribution q(x). Accordingly, the right side of the Equation 37 does not depend on the formation of a test distribution.

[Equation 36]

$$\theta^* = \underset{\theta}{\operatorname{argmax}} \log p(y \mid \theta) \quad (36)$$

[Equation 37]

$$\log p(y \mid \theta) = -F(q(x), \theta) + KL[q(x) \mid p(x \mid y, \theta)] \quad (37)$$

Equation 39 is established from Equation 38. The right side of the Equation 39 shows that a minimum −log p(y|θ) is achieved if KL[q(x)|p(x|y,θ)]=0, specifically if q(x)=p(x|y,θ) is satisfied. Specifically, a parameter to maximize a log-likelihood can be expressed by the following Equation 40.

[Equation 38]

$$F(q(x), \theta) = -\log p(y \mid \theta) + KL[q(x) \mid p(x \mid y, \theta)] \quad (38)$$

[Equation 39]

$$\min_{q(x)} F(q(x), \theta) \min_{q(x)} \{-\log p(y \mid \theta) + KL[q(x) \mid p(x \mid y, \theta)]\} \quad (39)$$

[Equation 40]

$$\theta^* = \underset{\theta}{\operatorname{argmax}} \log p(y \mid \theta) \quad (40)$$

$$= \underset{\theta}{\operatorname{argmax}} \left[ -\min_{q(x)} F(q(x), \theta) \right]$$

$$= \underset{\theta}{\operatorname{argmin}} \left[ \min_{q(x)} F(q(x), \theta) \right]$$

It is thus seen that maximum likelihood estimation can be made by minimizing the free energy in the left side with respect to the test distribution q(x) and then minimizing the free energy with respect to the parameter θ. A method can be devised from this fact that maximizes free energy with respect to the test distribution q(x) and the parameter θ instead of maximizing a log-likelihood.

To obtain Equation 41, two steps shown in Equation 42 are repeated.

An optimum value of the test distribution q(x) is given from the posterior distribution p(x|y,θ), whereas analytical calculation of a posterior distribution is generally difficult. In response, a candidate for q(x) is limited to enable optimization.

[Equation 41]

$$\{\hat{\theta}, \hat{q}(x)\} = \underset{\{\theta, q(x)\}}{\arg\min} F(q(x), \theta) \quad (41)$$

[Equation 42]

$$\bar{\theta}_{n+1} = \underset{\theta}{\arg\min} F(\bar{q}_n(x), \theta) \quad (42)$$

$$\bar{q}(x)_{n+1} = \underset{q(x)}{\arg\min} F(q(x), \bar{\theta}_{n+1})$$

Independence given in the following Equation 43 was assumed. While this assumption is given, the following Equation 44 is established that adopts alternate optimization.

A solution of Equation 45 can be obtained analytically by the variational method. A solution of Equation 46 cannot be obtained analytically, so that the Gaussian distribution given in the following Equation 47 or the gamma distribution given in the following Equation 48 is assumed as $q(x_j^{\{k\}})$.

[Equation 43]

$$q(X, Z, B) = \prod_{k=1}^{K} \prod_{j=1}^{J} q(x_j^{(k)}) q(z_j^{(k)}, b_j^{(k)}) \quad (43)$$

[Equation 44]

$$\bar{q}(X) = \underset{q(X)}{\arg\min} F(q(X)\bar{q}(Z, B), \bar{\theta}) \quad (44)$$

[Equation 45]

$$\bar{q}(z_j^{(k)}, b_j^{(k)}) = \arg\underset{q(z_j^{(k)}, b_j^{(k)})}{\min} F$$

$$\left(\bar{q}(X)\left[\prod_{k'=1}^{K}\prod_{j'=1}^{J}\bar{q}(z_{j'}^{(k')}, b_{j'}^{(k')})\right](\bar{q}(z_j^{(k)}, b_j^{(k)}))^{-1} q(z_j^{(k)}, b_j^{(k)}), \bar{\theta}\right) \quad (45)$$

$$(j = 1, \ldots, J) (k = 1, \ldots, K)$$

[Equation 46]

$$\bar{q}(X) = \underset{q(X)}{\arg\min} F(q(X)\bar{q}(Z, B), \bar{\theta}) \quad (46)$$

[Equation 47]

$$q(x_j^{(k)}) = N(x_j^{(k)}; \mu_j^{(k)}, (\sigma_j^{(k)})^2) \quad (47)$$

[Equation 48]

$$q(x_j^{(k)}) = (x_j^{(k)})^{\rho_{cd}-1} \frac{\exp(-x_j^{(k)}/\omega_{cd})}{\Gamma(\rho_{cd})\omega_{cd}^{\rho_{cd}}} \quad (48)$$

As a result, Equation 49 can be evaluated analytically. In the Equation 49, a parameter $(q(x_i^{\{k\}})$ of q(x) can be optimized by the non-linear optimization method such as the conjugate gradient method with respect to average μ and dispersion $\sigma^2$ in compliance with the Gaussian distribution, or with respect to a parameter $(\rho_{cd}, \omega_{cd})$ in compliance with the gamma distribution. The gamma distribution has preferable characteristics that enable expression of the non-negativity of x.

[Equation 49]

$$F(q(X)\bar{q}(Z,B),\bar{\theta}) \quad (49)$$

Industrial Applicability

The present invention is usefully applicable for X-ray CT devices for medical purposes and industrial purposes. One important application of the present invention relates to medical images, particularly, X-ray CT on hearts. Further, while a tiny object is to be measured during a nondestructive test for industrial purposes, minute motion of a stage becomes troublesome or deformation of a fluid becomes troublesome in the presence of such a fluid. Thus, the reduction in motion artifacts achieved by the present invention is expected to be applied usefully for various purposes.

The invention claimed is:

1. A motion tracking X-ray CT image processing method that sets previous knowledge about an X-ray absorption coefficient of a measuring target and makes statistical estimation, the method comprising:
   setting a first probability distribution showing the previous knowledge and setting a second probability distribution showing an X-ray projection image that is most likely to be observed with respect to the X-ray absorption coefficient of the measuring target, the first and second probability distributions being set when the measuring target changes smoothly with time;
   making statistical estimation depending on both the first and second probability distributions; and
   reconstructing an image based on the statistical estimation.

2. The motion tracking X-ray CT image processing method according to claim 1, wherein
   the first probability distribution is expressed by a probability distribution characterized by a parameter defined for each pixel of the reconstructed image, the parameter expressing a degree of temporal continuity of the reconstructed image, and
   when the reconstructed image is a known image, the second probability distribution is expressed by a probability distribution that describes a projection image expected to be observed from the reconstructed image.

3. The motion tracking X-ray CT image processing method according to claim 2, wherein the first probability distribution is further expressed by spatial correlation between neighboring pixels of the reconstructed image.

4. The motion tracking X-ray CT image processing method according to claim 2, wherein the first probability distribution is further expressed by a probability distribution showing that each pixel value of the reconstructed image is likely to take on a specific value depending on a tissue and a probability distribution showing that a tissue is also displaced temporally continuously.

5. A motion tracking X-ray CT image processing method that sets previous knowledge about an X-ray absorption coefficient expressed based on the characteristics of multiple tissues forming a measuring target and makes statistical estimation, the characteristics including continuity of a motion, the method comprising:

setting a first probability distribution showing the previous knowledge and setting a second probability distribution showing an X-ray projection image that is most likely to be observed with respect to the X-ray absorption coefficient of the measuring target, the first and second probability distributions being set when the measuring target changes smoothly with time;

making a statistical estimation depending on both the first and second probability distributions; and reconstructing an image based on the statistical estimation.

6. The motion tracking X-ray CT image processing method according to claim 5, wherein the first probability distribution is expressed by a probability distribution characterized by a parameter defined for each pixel of the reconstructed image, the parameter expressing a degree of temporal continuity of the reconstructed image, and when the reconstructed image is a known image, the second probability distribution is expressed by a probability distribution that describes a projection image expected to be observed from the reconstructed image.

7. The motion tracking X-ray CT image processing method according to claim 6, wherein the first probability distribution is further expressed by spatial correlation between neighboring pixels of the reconstructed image.

8. The motion tracking X-ray CT image processing method according to claim 6, wherein the first probability distribution is further expressed by a probability distribution showing that each pixel value of the reconstructed image is likely to take on a specific value depending on a tissue and a probability distribution showing that a tissue is also displaced temporally continuously.

9. A motion tracking X-ray CT image processing method comprising:

1) entering measuring conditions including a projection image and at least an X-ray intensity;

2) defining a physical process about photons observed in the projection image by a probability distribution;

3) defining a first probability distribution relating to a motion of a measuring target by a first probability distribution when the measuring target changes smoothly with time, the probability distribution being expressed by a parameter that expresses a degree of temporal continuity of the measuring target;

4) defining a second probability distribution relating to observation by a probability distribution describing a projection image expected to be observed from the reconstructed image; and 5) reconstructing an image and estimating a tissue class by estimating an expectation of a posterior probability (Bayesian estimation) or by estimating maximization of a posterior probability (MAP estimation) depending on both the first and second probability distributions.

10. A motion tracking X-ray CT image processing device that sets previous knowledge about an X-ray absorption coefficient of a measuring target and makes statistical estimation, the device comprising:

a computer having a program which upon execution sets a first probability distribution showing the previous knowledge and a second probability distribution showing an X-ray projection image that is most likely to be observed with respect to the X-ray absorption coefficient of the measuring target, the first and second probability distributions being set when the measuring target changes smoothly with time; and the program upon execution by the computer making a statistical estimation depending on both the first and second probability distributions, and reconstructing an image based on the statistical estimation.

11. The motion tracking X-ray CT image processing device according to claim 10, wherein the first probability distribution is expressed by a probability distribution characterized by a parameter defined for each pixel of a reconstructed image, the parameter expressing a degree of temporal continuity of the reconstructed image, and when the reconstructed image is a known image, the second probability distribution is expressed by a probability distribution that describes a projection image expected to be observed from the reconstructed image.

12. The motion tracking X-ray CT image processing device according to claim 10, wherein the first probability distribution is further expressed by spatial correlation between neighboring pixels of the reconstructed image.

13. The motion tracking X-ray CT image processing device according to claim 10, wherein the first probability distribution is further expressed by a probability distribution showing that each pixel value of the reconstructed image is likely to take on a specific value depending on a tissue and a probability distribution showing that a tissue is also displaced temporally continuously.

* * * * *